US007504431B2

(12) United States Patent
Hangeland et al.

(10) Patent No.: US 7,504,431 B2
(45) Date of Patent: Mar. 17, 2009

(54) SULFONYL AMIDE INHIBITORS OF CALCIUM CHANNEL FUNCTION

(75) Inventors: Jon J. Hangeland, Morrisville, PA (US); Daniel L. Cheney, Ringoes, NJ (US); Todd J. Friends, Bordentown, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 313 days.

(21) Appl. No.: 11/107,218

(22) Filed: Apr. 15, 2005

(65) Prior Publication Data

US 2005/0245535 A1 Nov. 3, 2005

Related U.S. Application Data

(60) Provisional application No. 60/563,072, filed on Apr. 16, 2004.

(51) Int. Cl.
*A61K 31/40* (2006.01)
*C07D 209/04* (2006.01)
(52) U.S. Cl. .................. 514/428; 514/365; 514/415; 514/534; 548/203; 548/469; 548/530; 560/12
(58) Field of Classification Search .................. 514/365, 514/415, 428, 534; 548/203, 469, 503; 560/12
See application file for complete search history.

(56) References Cited

U.S. PATENT DOCUMENTS

| | | | |
|---|---|---|---|
| 6,423,729 B1 | 7/2002 | Kurihara et al. | |
| 7,053,212 B2 * | 5/2006 | Cameron et al. | ........... 544/58.1 |
| 2004/0029865 A1 * | 2/2004 | Acker et al. | ................. 514/218 |

FOREIGN PATENT DOCUMENTS

| | | |
|---|---|---|
| EP | 0 545 845 | 2/1996 |
| JP | 11-35483 | 2/1999 |
| WO | WO 99/23072 | 5/1999 |
| WO | WO 00/02455 | 1/2000 |
| WO | WO 00/15845 | 3/2000 |
| WO | WO 00/58278 | 10/2000 |
| WO | WO 00/59882 | 10/2000 |
| WO | WO 01/02561 | 1/2001 |
| WO | WO 01/05389 | 1/2001 |
| WO | WO 01/19845 | 3/2001 |
| WO | WO 01/83431 | 11/2001 |
| WO | WO 03/007953 | 1/2003 |

OTHER PUBLICATIONS

Kugita et al., 1965, CAS: 62:36580.*
Baylis, C. et al., "Comparison of L-Type and Mixed L- and T-Type Calcium Channel Blockers on Kidney Injury Caused by Deoxycorticosterone-Salt Hypertension in Rats", American Journal of Kidney Diseases, vol. 38, No. 6, pp. 1292-1297 (2001).
Bhattacharjee, A. et al., "T-Type Calcium Channels Facilitate Insulin Secretion by Enhancing General Excitability in the Insulin-Secreting β-Cell Line, INS-1", Endocrinology, vol. 138, No. 9,-pp. 3735-3740 (1997).
Bilici, D. et al., "Protective Effect of T-Type Calcium Channel Blocker in Histamine-Induced Paw Inflammation in Rat", Pharmacological Research, vol. 44, No. 6, pp. 527-531 (2001).
Catterall, W.A. et al., "Structure and Regulation of Voltage-Gated $Ca^{2+}$ Channels", Annu. Rev. Cell Dev. Biol., vol. 16, pp. 521-555 (2000).
Chemin, J. et al., "Specific contribution of human T-type calcium channel isotypes ($α_{1G}$, $α_{1H}$ and $α_{1I}$) to neuronal excitability", Journal of Physiology, vol. 540 (Pt. 1), pp. 3-14 (2002).
Clozel, J.-P. et al., "Voltage-Gated T-Type $Ca^{2+}$ Channels and Heart Failure", Proceedings of the Association of American Physicians, vol. 111, No. 5, pp. 429-437 (1999).
Glasser, S.P., "The Relevance of T-Type Calcium Antagonists: A Profile of Mibefradil", Journal of Clinical Pharmacology, vol. 38, pp. 659-669 (1998).
Harada, K. et al., "Clinical Efficacy of Efonidipine Hydrochloride, a T-type Calcium Channel Inhibitor, on Sympathetic Activities: Examination Using Spectral Analysis of Heart Rate/Blood Pressure Variabilities and $^{123}$I-Metaiodobenzylguanidine Myocardial Scintigraphy", Circ. J., vol. 67, pp. 139-145 (2003).
Hayashi, K. et al., "Effect of Efonidipine and ACE Inhibitors on Proteinuria in Human Hypertension With Renal Impairment", American Journal of Hypertension, vol. 16, No. 2, pp. 116-122 (2003).
Honda, M. et al., "Divergent renal vasodilator action of L- and T-type calcium antagonists in vivo", Journal of Hypertension, vol. 19, No. 11, pp. 2031-2037 (2001).
Karam, H. et al., "Contrasting Effects of Selective T- and L-Type Calcium Channel Blockade on Glomerular Damage in DOCA Hypertensive Rats", Hypertension, vol. 34, pp. 673-678 (1999).
Kochegarov, A.A., "Therapeutical application of voltage-gated calcium channel modulators", Expert Opin. Ther. Patents, vol. 12, No. 2, pp. 243-287 (2002).
Mason, R.P. et al., "Antioxidant and Cytoprotective Activities of the Calcium Channel Blocker Mibefradil", Biochemical Pharmacology, vol. 55, pp. 1843-1852 (1998).
Min, J.-Y. et al., "Mibefradil Improves β-Andrenergic Responsiveness and Intracellular $Ca^{2+}$ Handling in Hypertrophied Rat Myocardium", Exp. Biol. Med., vol. 227, No. 5, pp. 336-344 (2002).

(Continued)

*Primary Examiner*—Rei-tsang Shiao
(74) *Attorney, Agent, or Firm*—Laurelee A. Duncan

(57) ABSTRACT

Compounds of formula I

I its stereoisomers, solvates, and salts, thereof, wherein: a, b, c, d, f, n, m and Ra are defined herein are are inhibitors of calcium channel function, and are useful in treating calcium channel-dependent disorders, including hypertension.

9 Claims, No Drawings

OTHER PUBLICATIONS

Mulder, P. et al., "Increased Survival After Long-Term Treatment With Mibefradil, a Selective T-Channel Calcium Antagonist, in Heart Failure", J. Am. Coll. Cardiol., vol. 29, No. 2, pp. 416-421 (1997).

Perez-Reyes, E., "Molecular Physiology of Low-Voltage-Activated T-type Calcium Channels", Physiol. Rev., vol. 83, pp. 117-161 (2003).

Qiu, C. et al., "Mibefradil prevents L-NAME-exacerbated nephrosclerosis in spontaneously hypertensive rats", Journal of Hypertension, vol. 17, No. 10, pp. 1489-1495 (1999).

Ramires, F.J.A. et al., "Myocardial Fibrosis Associated with Aldosterone or Angiotensin II Administration: Attenuation by Calcium Channel Blockade", J. Mol. Cell Cardiol., vol. 3, pp. 475-483 (1998).

Sandmann, S. et al., "L- and T-type calcium channel blockade—the efficacy of the calcium channel antagonist mibefradil", J. Clin. Basic Cardiol., vol. 2, pp. 187-201 (1999).

Tanaka, H. et al., "Efonidipine Hydrochloride: A Dual Blocker of L- and T-Type $Ca^{2+}$ Channels", Cardiovascular Drug Reviews, vol. 20, No. 1, pp. 81-92 (2002).

Villame, J. et al., "Effects of Mibefradil, a T- and L-Type Calcium Channel Blocker, on Cardiac Remodeling in the UM-X7.1 Cardiomyopathic Hamster", Cardiovascular Drugs and Therapy, vol. 15, pp. 41-48 (2001).

* cited by examiner

SULFONYL AMIDE INHIBITORS OF CALCIUM CHANNEL FUNCTION

This application claims priority from U.S. Provisional Application No. 60/563,072, filed Apr. 16, 2004, incorporated herein in its entirety by reference.

FIELD OF THE INVENTION

The present invention relates to sulfonyl amide compounds useful as inhibitors of calcium channel function, pharmaceutical compositions comprising said compounds, and methods of treating calcium channel-dependent disorders including hypertension.

BACKGROUND OF THE INVENTION

Calcium channels convert electrical signals in the cell membrane into an increase in intracellular calcium, thereby activating many crucial physiological processes, including muscle contraction, hormone secretion, neurotransmission, synaptic plasticity, regulation of enzymatic activites and gene expression. Calcium channels can be classified into a number of types and subtypes, for example L-(or $Ca_v1$), P/Q-(or $Ca_v2.1$), N-(or $Ca_v2.2$), R-($Ca_v2.3$) and T-(or $Ca_v3$) types. T-type calcium channels can, for example, be subclassified into α1G (or Cav3.1), α1H (or $Ca_v3.2$), and α1I (or Cav 3.3) T channels. See e.g. Catterall, *Annu. Rev. Cell Dev. Biol.* 16, 521-55, (2000) and Perez-Reyes *Physiol. Rev.* 83, 117-161, (2003).

Physiologically, calcium channels are distributed widely. For example T-type channels can be found in neurons, the heart, kidney, smooth muscle, skeletal muscle, sperm, and endocrine tissues (such as adrenal and pituitary glands and the pancreas). Consequently, T-type calcium channels are thought to be involved in autonomic nervous functions, and in regulation of cardiovascular activities such as heart rate, arterial and venous smooth muscle innervation and tone, pulmonary rate, and other critical processes.

Due to their role in modulating many physiological processes, abnormal or unwanted calcium channel activity is also associated with many disease states. Agents which antagonize or agonize the activity of calcium channels have been shown to be useful as therapies for treating a wide variety of diseases and disorders. See e.g., WO 99/23072, EP 0545845, and Kochegarov, *Expert Opin. Ther. Patents*, 12, 243-287, (2002).

L-channel blockers have a well established role in the treatment of diseases such as hypertension and angina (see e.g. Mannhold, *Drugs of Today*, 30, 103-122, 1994). Compounds that have exclusively or predominantly T-channel blocking activity or that have dual L- and T-channel blocking activities are considered to be useful for the treatment of hypertension, angina, arrhythmia, congestive heart failure, renal disease, epilepsy, neuropathic pain, and other diseases and conditions. See e.g., Perez-Reyes *Physiol. Rev.* 83, 117-161, 2003 and WO 03/07953.

T-channel blockers are also useful for the treatment of sleep disorders, mood disorders, depression, migrane headache, neuronal excitability disorders, hyperaldosteronemia, preterm labor, urinary incontinence, brain aging, or neurodegenerative related diseases such as Alzheimer's disease. See e.g., WO 01/02561; WO 00/02455; JP11035483; and Chemin, *J. Physiol.*, 540, 3-14, (2002). Additionally, T-type calcium channels play a role in pancreatic beta-cell insulin secretion. Therefore, T-type blockers may be useful for treatment of hypo- and hyperinsulinemia and the treatment and/or prevention of type 1 and type 2 diabetes as well as microvascular or macrovascular diseases associated with diabetes. See, e.g., Bhattacharjee, *Endocrinology*, 138, 3735-40, (1997), and WO 00/15845. T-type calcium channel blockers may also be useful in the treatment of cancer. See e.g., WO 00/59882 and WO 2001019845.

Drugs such as mibefradil and efonidipine which potently block both T and L calcium channels have been shown to be useful or potentially useful in a variety of disease states. Such drugs may have therapeutic advantages over calcium channel blockers that predominantly target the L-channel. For example, mibefradil was shown to be useful for the treatment of hypertension and angina and did not show negative inotropy, reflex tachycardia, vasoconstrictive hormone release or peripherial edema, side-effects shown by predominant L-channel blockers (see eg Sandman, *J. Clin. Basic Cardiol.*, 2, 187-201, 1999 and Glasser, *J. Clin. Pharmacol.*, 38, 659-669, 1998). Also mibefradil has been shown to be potentially cardioprotective (see e.g. Villame, *Cardiovascular Drugs and Therapy*, 15, 41-48, 2001; Ramires, *J. Mol. Cell Cardiol.*, 30, 475-483, 1998) and renal protective (see e.g. Honda, *J. Hypertension*, 19, 2031-2037, 2001; Baylis, *Am. J. Kidney Dis.*, 38, 1292-1297, 2001; Qiu, *J. Hypertension*, 1489-1495, 1999; and Karam, *Hypertension*, 34, 673-678, 1999), which would be advantageous in the treatment of hypertension. Also, unlike most predominant L-channel blockers, mibefradil has been shown to be potentially useful in the treatment of heart failure (see e.g. Clozel, *Proceedings of the Association of American Physicians*, 111, 429-437, 1999; Mulder, *Journal of the American College of Cardiology*, 29, 416, 1997; Meissner, *Exp. Biol. Med* 227, 336-44, 2002). Mibefradil may also be useful in the treatment of atherosclerosis (see e.g. Mason, *Biochemical Pharmacology*, 55, 1843-1852, 1998) and inflammation (see e.g. Bilici, *Pharmacological Research*, 527-531, 2001). Efonidipine, another calcium channel blocker with a combination of T- and L-channel blocking activities also shows therapeutic advantages over pure L-channel blockers (see e.g. Harada, *Circ. J.* 67, 139-145, 2003; Hayashi, *Amer. Heart J.*, 16, 116-122, 2003; Tanaka, *Cardiovascular Drug Reviews*, 20, 81-92, 2002).

SUMMARY OF THE INVENTION

The present invention provides dihydropyrimidone compounds, pharmaceutical compositions containing such dihydropyrimidone compounds, and methods for treating calcium channel-dependent disorders using such compounds and compositions. Specifically, the invention provides compounds of Formula I:

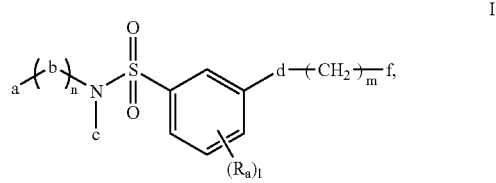

its stereoisomers, solvates, and salts, thereof wherein:
a is $R^1$, >$C_3$alkyl, substituted alkyl, cycloalkyl, heterocyloalkyl, aryl, or heteroaryl (preferably $R^1$, $C_{4-8}$alkyl, or aryl);
$R^1$ is —$C(O)NR^2R^3$ or $C(O)OR^4$—;
$R^2$ and $R^3$ are independently
  (a) hydrogen;
  (b) alkyl, substituted alkyl, cycloalkyl, aryl, heterocyclo, heteroaryl, (aryl)alkyl, (cycloalkyl)alkyl, (heterocyclo)alkyl, or (heteroaryl)alkyl; or
  (c) $R^2$ and $R^3$ together to the atom to which they are attached form a heterocycle;

b is $CR^{13}R^{14}$ (especially where $R^{13}$ and $R^{14}$ are, independently hydrogen or $C_{1-4}$alkyl);

c is aryl or heteroaryl;

d is a bond, alkylene, —OC(=O)—, —C(=O)—, —C(=O)O—, —C(=O)NR$^7$—, —NR$^7$—, —S(=O)—, —SO$_2$—, —SO$_2$NR$^7$—, —NR$^7$S(O)$_2$NR$^8$—, —NR$^7$S(O)$_2$—, —NR$^7$C(=O)—, —NR$^7$C(=O)O—, and —NR$^7$C(=O)NR$^8$—;

f is hydrogen, halogen, nitro, cyano, alkyl, substituted alkyl, aryl, heteroaryl, cycloalkyl, heterocyclo, —O(CH$_2$)$_p$R$^6$, —S(CH$_2$)$_p$R$^6$, —OC(=O)(CH$_2$)$_q$R$^6$, —C(=O)(CH$_2$)$_q$R$^6$, —C(O)O(CH$_2$)$_p$R$^6$, —C(=O)NR$^{11}$R$^{12}$, —NR$^{11}$R$^{12}$, —S(=O)(CH$_2$)$_p$R$^6$, —SO$_2$(CH$_2$)$_q$R$^6$, —SO$_2$NR$^{11}$R$^{12}$, —NR$^{10}$SO$_2$NR$^{11}$R$^{12}$, —NR$^{10}$SO$_2$(CH$_2$)$_q$R$^6$, —NR$^{10}$C(=O)(CH$_2$)$_q$R$^6$, —NR$^{10}$C(O)O(CH$_2$)$_p$R$^6$, or —NR$^{10}$C(=O)NR$^{11}$R$^{12}$;

$R^4$, $R^5$, $R^6$, $R^7$, $R^8$, $R^9$, $R^{11}$ and $R^{12}$ are independently hydrogen; alkyl, substituted alkyl, cycloalkyl, aryl, heterocyclo, heteroaryl, (aryl)alkyl, (cycloalkyl)alkyl, (heterocyclo)alkyl, or (heteroaryl)alkyl;

or $R^{11}$ and $R^{12}$ together to the atom to which they are attached form a heterocycle;

l, m, n, p and q are independently 0 to 4;

$R_a$, $R^{13}$ and $R^{14}$ are independently where valence allows hydrogen, cyano, nitro, halogen, oxo, alkyl, substituted alkyl, aryl, heteroaryl, cycloalkyl, heterocyclo, —OR$^{15}$, —SR$^{15}$, —OC(=O)R$^{15}$, —C(=O)R$^{15}$, —CO$_2$R$^{15}$, —C(=O)NR$^{16}$R$^{17}$, —NR$^{16}$R$^{17}$, —S(=O)R$^{15}$, or —SO$_2$R$^{15}$;

or $R^{13}$ and $R^{14}$ are taken together to form oxo;

$R^{15}$, $R^{16}$ and $R^{17}$ are independently hydrogen, alkyl, substituted alkyl, cycloalkyl, aryl, heterocyclo, heteroaryl, (aryl)alkyl, (cycloalkyl)alkyl, (heterocyclo)alkyl, or (heteroaryl)alkyl; and $R^{21}$ and $R^{22}$ are independently hydrogen or $C_{1-4}$alkyl;

provided that when c is phenyl and $R_a$ is located para to the sulfoxide substituent; $R_a$ is not chloro or —OMe; and when a is >$C_3$ alkyl, n is 0.

This invention is also directed to pharmaceutical compositions comprising at least one compound of formula (I) and a pharmaceutically acceptable vehicle, carrier or diluent.

This invention is also directed to methods of treating a mammalian host to relieve one or more calcium channel-dependent disorders, including hypertension (wherein the blood pressure of a hypertensive mammalian host is reduced), comprising administering to said host in need of such treatment an effective amount of a pharmaceutical composition comprising a compound of formula (I).

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, >$C_3$alkyl refers to straight and branched chain alkyl groups having greater than 3 carbon atoms and "$C_{4-8}$alkyl" refers to straight and branched chain alkyl groups with four to eight carbon atoms, such as n-butyl, t-butyl, 3,3 dimethyl 1-propyl, n-pentyl, s-hexyl and so forth.

The subscript "0" refers to a bond. Thus, the term hydroxy ($C_{0-2}$)alkyl or ($C_{0-2}$)hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O) R$_b$, SO$_3$H, —PO(OH)$_2$, —C(=O)R$_a$, —CO$_2$R$_a$, —C(=O) NR$_a$R$_b$, —C(=O)($C_{1-4}$alkylene)NR$_a$R$_b$, —C(=O)NR$_a$ (SO$_2$)R$_b$, —CO$_2$($C_{1-4}$alkylene)NR$_a$R$_b$, —NR$_a$C(=O)R$_b$, —NR$_a$CO$_2$R$_b$, —NR$_a$($C_{1-4}$alkylene)CO$_2$R$_b$, =N—OH, =N—O-alkyl, aryl, cycloalkyl, heterocyclo, and/or heteroaryl, wherein R$_a$ and R$_b$ are selected from hydrogen, alkyl, alkenyl, CO$_2$H, CO$_2$(alkyl), $C_{3-7}$cycloalkyl, phenyl, benzyl, phenylethyl, napthyl, a four to seven membered heterocylo, or a five to six membered heteroaryl, or when attached to the same nitrogen atom may join to form a heterocyclo or heteroaryl, and R$_c$ is selected from same groups as R$_a$ and R$_b$ but is not hydrogen. Each group R$_a$ and R$_b$ when other than hydrogen, and each R$_c$ group optionally has up to three further substituents attached at any available carbon or nitrogen atom of R$_a$, R$_b$, and/or R$_c$, said substituent(s) being selected from the group consisting of ($C_{1-6}$)alkyl, ($C_{2-6}$)alkenyl, hydroxy, halogen, cyano, nitro, CF$_3$, O($C_{1-6}$alkyl), OCF$_3$, C(=O)H, C(=O)($C_{1-6}$alkyl), CO$_2$H, CO$_2$($C_{1-6}$alkyl), NHCO$_2$($C_{1-6}$ alkyl), —S($C_{1-6}$alkyl), —NH$_2$, NH($C_{1-6}$alkyl), N($C_{1-6}$ alkyl)$_2$, N(CH$_3$)$_3^+$, SO$_2$($C_{1-6}$alkyl), C(=O)($C_{1-4}$alkylene) NH$_2$, C(=O)($C_{1-4}$alkylene)NH(alkyl), C(=O)($C_{1-4}$alkylene)N($C_{1-4}$alkyl)$_2$, $C_{3-7}$cycloalkyl, phenyl, benzyl, phenylethyl, phenyloxy, benzyloxy, napthyl, a four to seven membered heterocylo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl ($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "alkoxy" refers to an alkyl or substituted alkyl group as defined above having one or two oxygen atoms (—O—) in the alkyl chain. For example, the term "alkoxy" includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$alkyl, and so forth.

The term "thioalkyl" or "alkylthio" refers to an alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an alkyl or substituted alkyl group as defined above having one or two nitrogen (—NR—) atoms in the alkyl chain. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —$CH_2$—$NH_2$, —NH—$CH_3$, —$(CH_2)_2$—$NH_2$, —NH—$CH_2$—$CH_3$, —$CH_2$—$NH_2$—$CH_3$, and —N—$(CH_3)_2$. A lower aminoalkyl comprises an aminoalkyl having one to four carbon atoms. "Amino" refers to the group $NH_2$.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

It should be understood that the selections for alkoxy, thioalkyl, and aminoalkyl will be made by one skilled in the field to provide stable compounds. Thus, for example, in compounds of formula (I), when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "amide" or "amidyl" refers to the group C(=O) $NR_aR_b$, wherein the groups $R_a$ and $R_b$ are defined as recited above in the definition for substituted alkyl groups.

The term "sulfonyl" refers to a sulphoxide group linked to an organic radical in compounds of formula (I), more particularly, the monovalent group $S(O)_{1-2}$—$R_e$, or the bivalent group —$S(O)_{1-2}$— linked to organic radicals in compounds of formula (I). Accordingly, in compounds of formula (I), when it is recited that G can be "sulfonyl," this is intended to encompass a selection for G of —S(=O)— or —$SO_2$— as well as the groups —S(=O)$R_e$—, —$R_eS$(=O)—, —$SO_2R_e$—, or —$R_eSO_2$—, wherein in this instance, the group $R_e$ will be selected from those recited above for acyl and alkoxycarbonyl groups.

The term "sulfonamidyl" refers to the group —$S(O)_2$ $NR_aR_b$, wherein $R_a$ and $R_b$ are as defined above for substituted alkyl groups. Additionally, the sulfonamidyl group may be bivalent, in which case one of the groups $R_a$ and $R_b$ will be a bond. Thus, in compounds of formula (I), when it is stated that G may be sulfonamidyl, it is intended to mean that G is a group —$S(O)_2NR_a$—.

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC$(=O)$R_b$, $SO_3H$, —PO $(OH)_2$, —C(=O)$R_a$, —$CO_2R_a$, —C(=O)$NR_aR_b$, —C(=O) $(C_{1-4}$alkylene)$NR_aR_b$, —C(=O)$NR_a(SO_2)R_b$, —$CO_2(C_{1-4}$alkylene)$NR_aR_b$, —$NR_aC$(=O)$R_b$, —$NR_aCO_2R_b$, —$NR_a$ $(C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, O($C_{1-4}$alkyl), $OCF_3$, C(=O)H, C(=O)($C_{1-4}$alkyl), $CO_2H$, $CO_2$($C_{1-4}$alkyl), $NHCO_2$($C_{1-4}$ alkyl), —S($C_{1-4}$alkyl), —$NH_2$, NH($C_{1-4}$alkyl), N($C_{1-4}$ alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O) ($C_{1-4}$alkylene)N($C_{1-4}$alkyl)$_2$.

Accordingly, in compounds of formula (I), the term "cycloalkyl" includes cyclopropyl, cyclobutyl, cyclopentyl, cyclohexyl, cycloheptyl, cyclooctyl, etc., as well as the following ring systems,

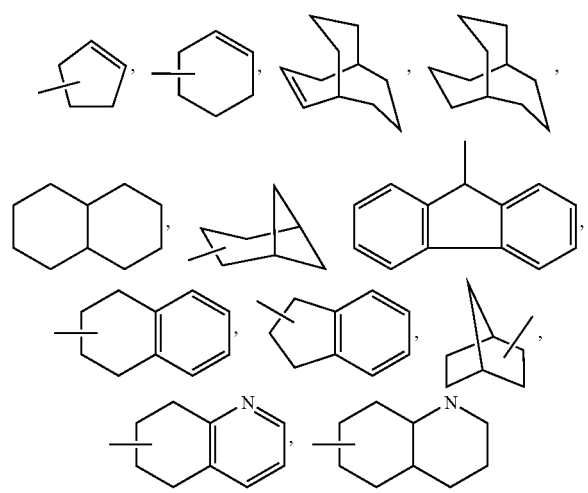

and the like, which optionally may be substituted at any available atoms of the ring(s). Preferred cycloalkyl groups include cyclopropyl, cyclobutyl, cyclopentyl, cyclohexyl,

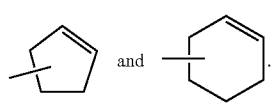

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Thus, examples of aryl groups include:

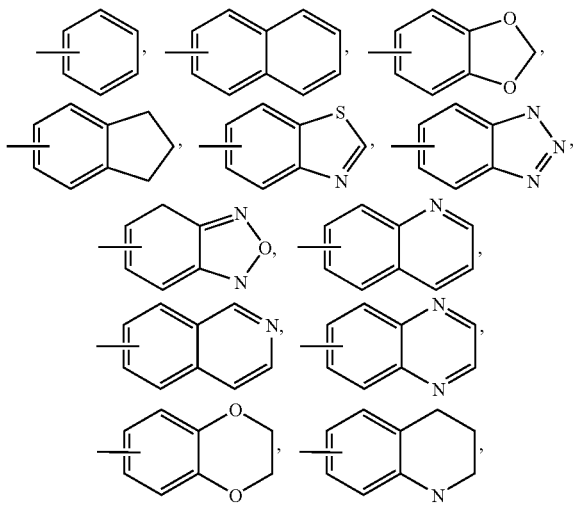

and the like, which optionally may be substituted at any available carbon or nitrogen atom. A preferred aryl group is optionally-substituted phenyl.

The terms "heterocyclo" or "heterocyclic" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

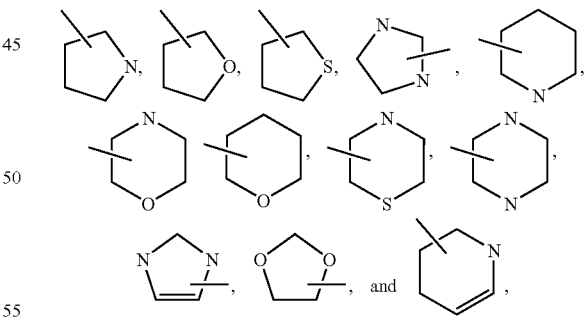

which optionally may be substituted.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $—NR_aR_b$, $—N(alkyl)_3^+$, $—NR_aSO_2$, $—NR_aSO_2R_c$, $—SO_2R_c$ $—SO_2NR_aR_b$, $—SO_2NR_aC(=O)R_b$, $SO_3H$, $—PO(OH)_2$, $—C(=O)R_a$, $—CO_2R_a$, $—C(=O)NR_aR_b$, $—C(=O)(C_{1-4}alkylene)NR_aR_b$, $—C(=O)NR_a(SO_2)R_b$, $—CO_2(C_{1-4}alkylene)NR_aR_b$, $—NR_aC(=O)R_b$, $—NR_aCO_2R_b$, $—NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})alkyl$, $(C_{2-4})alkenyl$, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $—S(C_{1-4}alkyl)$, $—NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

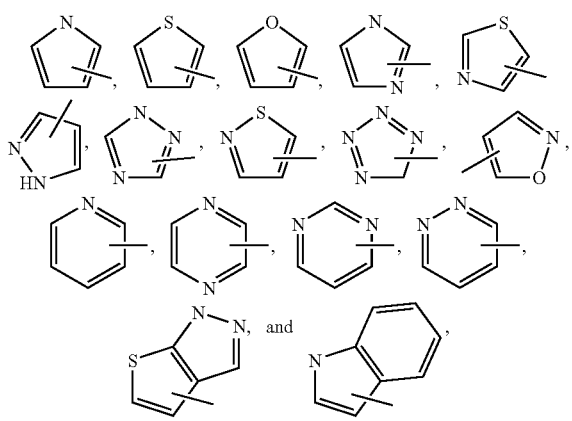

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates. Any tautomers which may exist are also contemplated herein as part of the present invention. Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, 1-38 (1992), each of which is incorporated herein by reference.

All stereoisomers of the present compounds, such as those which may exist due to asymmetric carbons on the R substituents, including enantiomeric forms (which may exist even in the absence of asymmetric carbons, e.g., atropisomers) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Preferred Compounds

Preferred compounds within the scope of Formula I (above), its stereoisomers, solvates and salts, thereof, are those having the following structure:

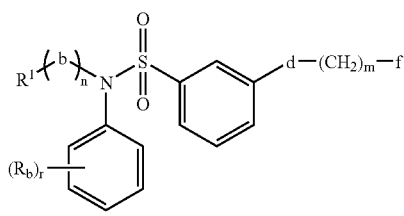

its stereoisomers, solvates, and salts, thereof, in which:

d is a bond, —N($R^7$)C((=O)—, —C((=O)N$R^7$—, —S(O)$_t$N$R^7$—, —N($R^7$) S(O)$_t$—, or —S(O)$_t$—;

m is 0, 1, 2 or 3; and $R_b$, is hydrogen, cyano, nitro, halogen, alkyl, substituted alkyl, aryl, heteroaryl, cycloalkyl, heterocyclo, —O$R^{18}$, —S$R^{18}$, —OC(=O)$R^{18}$, —C(=O)$R^{18}$, —CO$_2R^{18}$, —C(=O)N$R^{19}R^{20}$, —N$R^{19}R^{20}$, —S(=O)$R^{18}$, or —SO$_2R^{18}$;

$R^{18}$, $R^{19}$ and $R^{20}$ are independently hydrogen; alkyl, substituted alkyl, cycloalkyl, aryl, heterocyclo, heteroaryl, (aryl)alkyl, (cycloalkyl)alkyl, (heterocyclo)alkyl, or (heteroaryl)alkyl.

r is 0, 1, 2 or 3; and $R^{13}$ and $R^{14}$ are independently hydrogen or $CH_3$.

Other preferred compounds within the scope of Formula (I) have the structures:

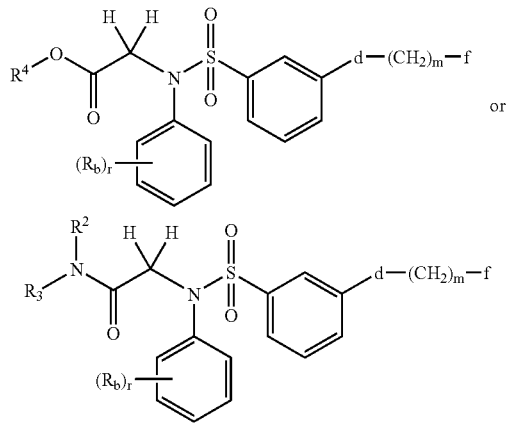

their stereoisomers, solvates, and salts, thereof in which:

$R^2$ is hydrogen or $C_{1-4}$alkyl;

$R^3$ is alkyl, cycloalkyl, heterocyclo, (cycloalkyl)alkyl, (heterocyclo)alkyl, or aminoalkyl; and $R^4$ is selected from hydrogen; alkyl, cycloalkyl, (aryl)alkyl, (cycloalkyl)alkyl, (heterocyclo)alkyl, and (heteroaryl)alkyl.

Other preferred compounds within the scope of formula I, its stereoisomers, solvates, and salts, thereof are those in which d is a bond, —N($R^7$)C((=O)—, or —C((=O)N$R^7$—.

Other preferred compounds within the scope of formula I, its stereoisomers, solvates, and salts, thereof are those in which f is:

(a) hydrogen, amino or nitro:

(b) alkyl, heteroaryl, or heterocyclo, each group of which is substituted, where valence allows, by 1-3 groups selected from hydrogen, cyano, nitro, halogen, oxo, alkyl, substituted alkyl, aryl, heteroaryl, cycloalkyl, heterocyclo, —O$R^{15}$ and —S$R^{15}$; or (c) —C(O)O(CH$_2$)$_p$R$^8$, —NR$^9$R$^{10}$, —O(CH$_2$)$_p$R$^7$, aryl —NR$^9$C(O)O(CH$_2$)$_p$R$^8$—, —NR$^9$C(=O)(CH$_2$)$_q$R$^8$, or —C(=O)NR$^9$R$^{10}$; and $R^{21}$ and $R^{22}$ are independently hydrogen or $CH_3$.

Other preferred compounds within the scope of formula I, its stereoisomers, solvates, and salts, thereof are those in which -d-(e)$_m$-f is selected from:

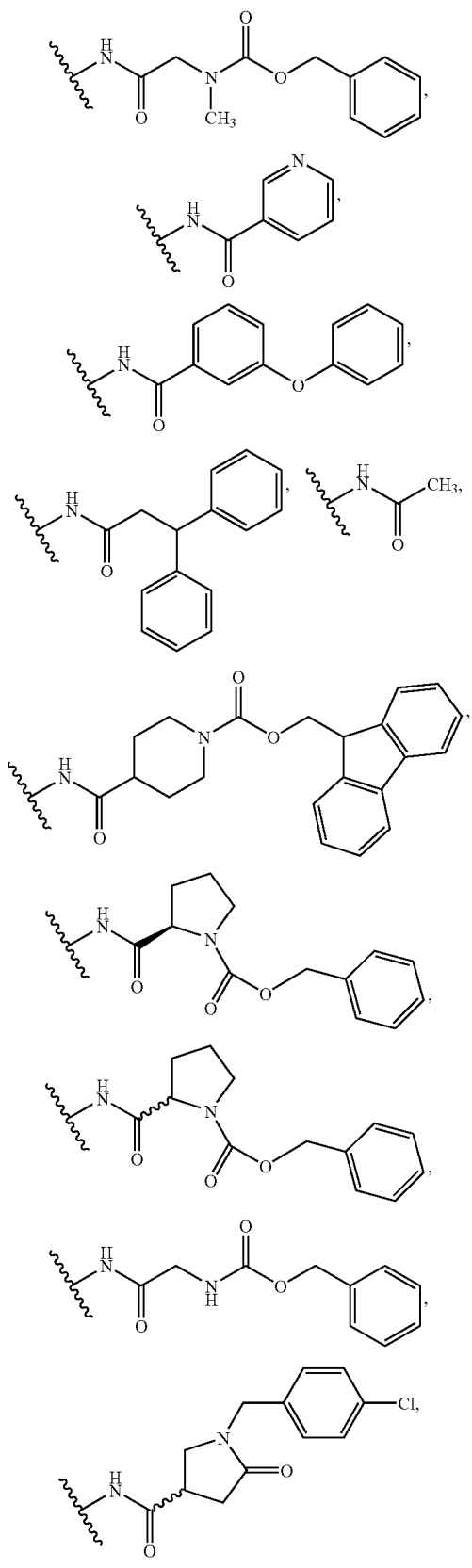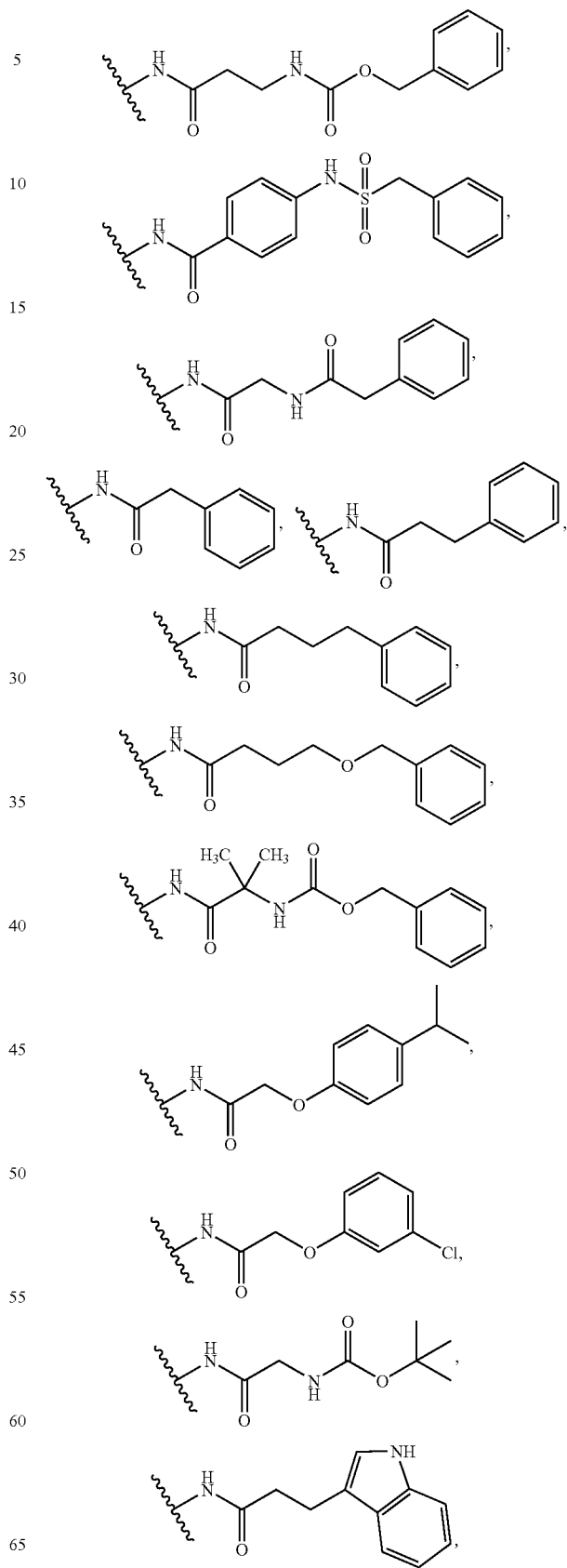

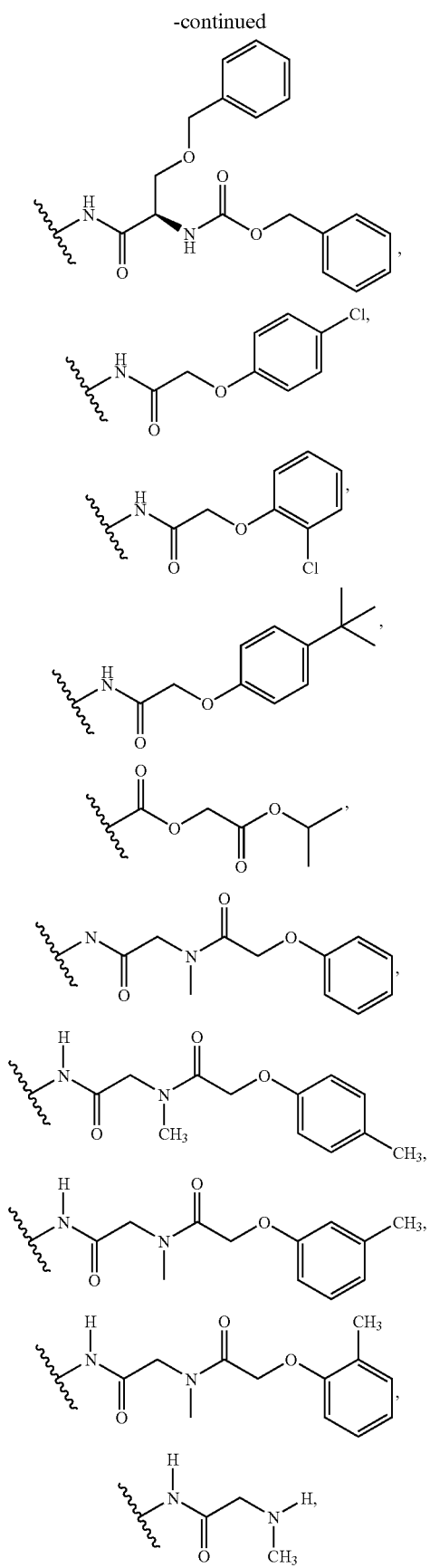
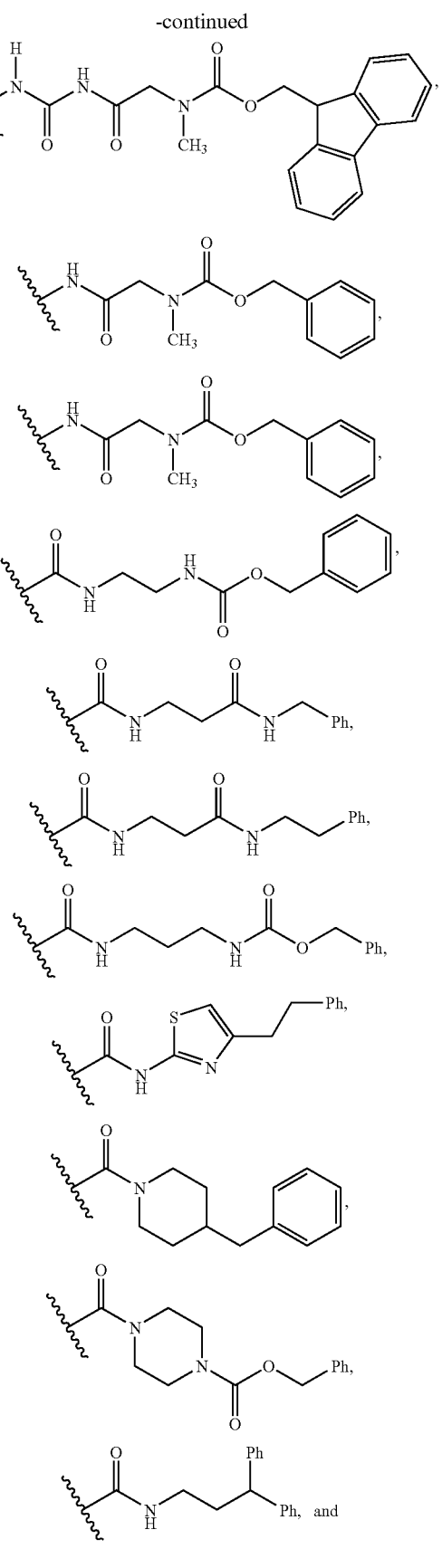

-continued

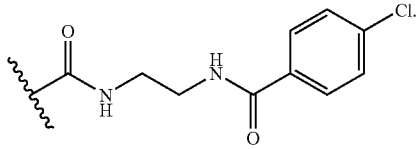

Other preferred compounds within the scope of Formula (I), its stereoisomers, solvates, and salts, thereof are those in which $R^1$-$(b)_m$-f is selected from:

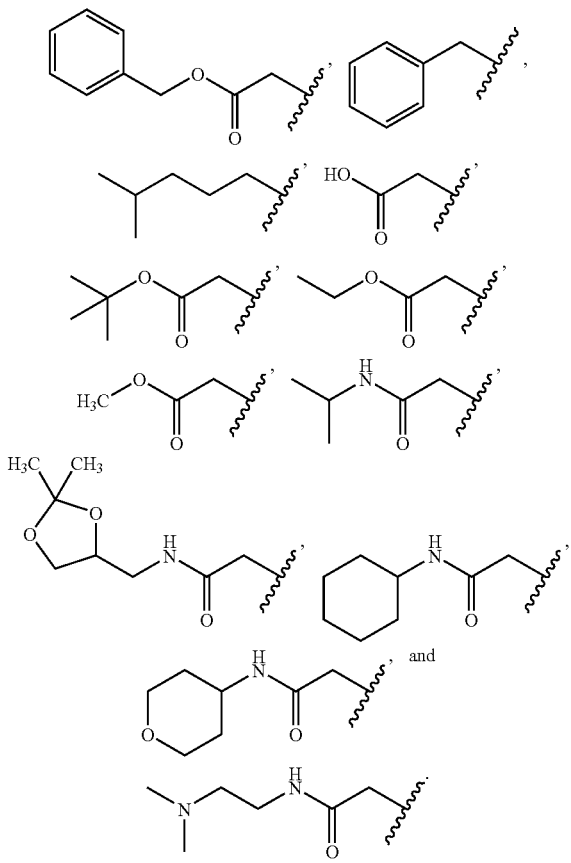

Other preferred compounds within the scope of Formula (I), its stereoisomers, solvates, and salts, thereof are those in which c is selected from:

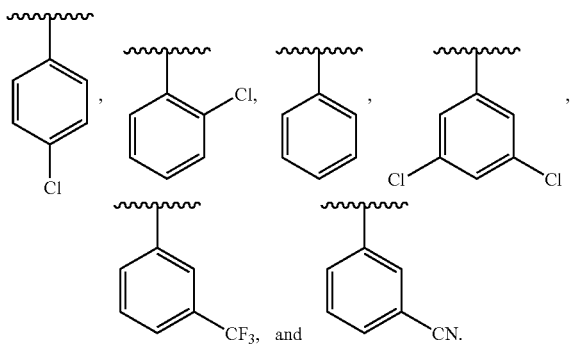

Other preferred compounds within the scope of formula I, its stereoisomers, solvates, and salts, thereof are those having the formula selected from:

Isopropyl{(3-chlorophenyl)[(3-nitrophenyl)sulfonyl]amino}acetate;
Isopropyl[[(3-aminophenyl)sulfonyl](3-chlorophenyl)amino]acetate;
Isopropyl[(3-chlorophenyl)({3-[(3-phenoxybenzoyl)amino]phenyl}sulfonyl)amino]acetate;
Isopropyl[(3-chlorophenyl)({3-[(3,3-diphenylpropanoyl)amino]phenyl}sulfonyl)amino]acetate;
Isopropyl[{[3-(acetylamino)phenyl]sulfonyl}(3-chlorophenyl)amino]acetate;
Isopropyl[(3-chlorophenyl)({3-[(pyridin-3-ylcarbonyl)amino]phenyl}sulfonyl)amino]acetate;
9H-Fluoren-9-ylmethyl4-{[(3-{[(3-chlorophenyl)(2-isopropoxy-2-oxoethyl)amino]sulfonyl}phenyl)amino]carbonyl}piperidine-1-carboxylate;
Benzyl(2R)-2-{[(3-{[(3-chlorophenyl)(2-isopropoxy-2-oxoethyl)amino]sulfonyl}phenyl)amino]carbonyl}pyrrolidine-1-carboxylate;
Benzyl(2S)-2-{[(3-{[(3-chlorophenyl)(2-isopropoxy-2-oxoethyl)amino]sulfonyl}phenyl)amino]carbonyl}pyrrolidine-1-carboxylate;
Isopropyl[{[3-({[[(benzyloxy)carbonyl](methyl)amino]acetyl}amino)phenyl]sulfonyl}(3-chlorophenyl)amino]acetate;
Isopropyl[({3-[({[(benzyloxy)carbonyl]amino}acetyl)amino]phenyl}sulfonyl)(3-chlorophenyl)amino]acetate;
Isopropyl[{[3-({[1-(4-chlorobenzyl)-5-oxopyrrolidin-3-yl]carbonyl}amino)phenyl]sulfonyl}(3-chlorophenyl)amino]acetate;
Isopropyl[({3-[(3-{[(benzyloxy)carbonyl]amino}propanoyl)amino]phenyl}sulfonyl)(3-chlorophenyl)amino]acetate;
Isopropyl[{[3-({4-[(benzylsulfonyl)amino]benzoyl}amino)phenyl]sulfonyl}(3-chlorophenyl)amino]acetate;
Isopropyl[(3-chlorophenyl)({3-[(pyridin-2-ylacetyl)amino]phenyl}sulfonyl)amino]acetate;
Isopropyl((3-chlorophenyl){[3-({[(phenylacetyl)amino]acetyl}amino)phenyl]sulfonyl}amino)acetate;
Isopropyl[(3-chlorophenyl)({3-[(phenylacetyl)amino]phenyl}sulfonyl)amino]acetate;
Isopropyl[(3-chlorophenyl)({3-[(3-phenylpropanoyl)amino]phenyl}sulfonyl)amino]acetate;
Isopropyl[(3-chlorophenyl)({3-[(4-phenylbutanoyl)amino]phenyl}sulfonyl)amino]acetate;
Isopropyl[[(3-{[4-(benzyloxy)butanoyl]amino}phenyl)sulfonyl](3-chlorophenyl)amino]acetate;
Isopropyl[({3-[(2-{[(benzyloxy)carbonyl]amino}-2-methylpropanoyl)amino]phenyl}sulfonyl)(3-chlorophenyl)amino]acetate;
Isopropyl{(3-chlorophenyl)[(3-{[(4-isopropylphenoxy)acetyl]amino}phenyl)sulfonyl]amino}acetate;
Isopropyl[[(3-{[(3-chlorophenoxy)acetyl]amino}phenyl)sulfonyl](3-chlorophenyl)amino]acetate;
Isopropyl[{[3-({[(tert-butoxycarbonyl)amino]acetyl}amino)phenyl]sulfonyl}(3-chlorophenyl)amino]acetate;
Isopropyl{(3-chlorophenyl)[(3-{[3-(1H-indol-3-yl)propanoyl]amino}phenyl)sulfonyl]amino}acetate;
Isopropyl[({3-[((2R)-3-(benzyloxy)-2-{[(benzyloxy)carbonyl]amino}propanoyl)amino]phenyl}sulfonyl)(3-chlorophenyl)amino]acetate;
Isopropyl[[(3-{[(4-chlorophenoxy)acetyl]amino}phenyl)sulfonyl](3-chlorophenyl)amino]acetate;
Isopropyl[[(3-{[(2-chlorophenoxy)acetyl]amino}phenyl)sulfonyl](3-chlorophenyl)amino]acetate;

Isopropyl[[(3-{[(4-tert-butylphenoxy)acetyl]amino}phenyl)sulfonyl](3-chlorophenyl)amino]acetate;
2-Isopropoxy-2-oxoethyl 3-{[(3-chlorophenyl)(2-isopropoxy-2-oxoethyl)amino]sulfonyl}benzoate;
Methyl[{[3-({[[(benzyloxy)carbonyl](methyl)amnino]acetyl}amino)phenyl]sulfonyl}(3-chlorophenyl)amino]acetate;
Ethyl[{[3-({[[(benzyloxy)carbonyl](methyl)amino]acetyl}amino)phenyl]sulfonyl}(3-chlorophenyl)amino]acetate;
tert-Butyl[{[3-({[[(benzyloxy)carbonyl](methyl)amino]acetyl}amino)phenyl]sulfonyl}(3-chlorophenyl)aamino]acetate;
Benzyl[{[3-({[[(benzyloxy)carbonyl](methyl)amino]acetyl}amino)phenyl]sulfonyl}(3-Benzyl{2-[(3-{[benzyl(3-chlorophenyl)amino]sulfonyl}phenyl)amino]-2-oxoethyl}methylcarbamate;
Benzyl{2-[(3-{[(3-chlorophenyl)(4-methylpentyl)amino]sulfonyl}phenyl)amino]-2-oxoethyl}methylcarbamate;
[{[3-({[[(Benzyloxy)carbonyl](methyl)amino]acetyl}amino)phenyl]sulfonyl}(3-chlorophenyl)amino]acetic acid;
tert-Butyl((3-chlorophenyl){[3-({[methyl(phenoxyacetyl)amino]acetyl}amino)phenyl]sulfonyl}amino)acetate;
tert-Butyl[(3-chlorophenyl)({3-[({methyl[(4-methylphenoxy)acetyl]amino}acetyl)amino]phenyl}sulfonyl)amino]acetate;
tert-Butyl[(3-chlorophenyl)({3-[({methyl[(3-methylphenoxy)acetyl]amino}acetyl)amino]phenyl}sulfonyl)amino]acetate;
tert-Butyl[(3-chlorophenyl)({3-[({methyl[(2-methylphenoxy)acetyl]amino}acetyl)amino]phenyl}sulfonyl)amino]acetate;
tert-Butyl((3-chlorophenyl){[3-({[[(9H-fluoren-9-ylmethoxy)carbonyl](methyl)amino]acetyl}amino)phenyl]sulfonyl}amino)acetate;
tert-Butyl{(3-chlorophenyl)[(3-{[(methylamino)acetyl]amino}phenyl)sulfonyl]amino}acetate;
3-{[(2-tert-Butoxy-2-oxoethyl)(3-chlorophenyl)amino]sulfonyl}benzoic acid;
tert-Butyl[{[3-({[3-(benzylamino)-3-oxopropyl]amino}carbonyl)phenyl]sulfonyl}(3-chlorophenyl)amino]acetate;
tert-Butyl[(3-chlorophenyl)({3-[({3-oxo-3-[(2-phenylethyl)amino]propyl}amino)carbonyl]phenyl}sulfonyl)amino]acetate;
tert-Butyl[[(3-{[(2-{[(benzyloxy)carbonyl]amino}ethyl)amino]carbonyl}phenyl)sulfonyl](3-chlorophenyl)amino]acetate;
tert-Butyl[[(3-{[(3-{[(benzyloxy)carbonyl]amino}propyl)amino]carbonyl}phenyl)sulfonyl](3-chlorophenyl)amino]acetate;
tert-Butyl((3-chlorophenyl){[3-({[4-(2-phenylethyl)-1,3-thiazol-2-yl]amino}carbonyl)phenyl]sulfonyl}amino)acetate;
tert-Butyl[({3-[(4-benzylpiperidin-1-yl)carbonyl]phenyl}sulfonyl)(3-chlorophenyl)amino]acetate;
tert-Butyl[({3-[({2-[(4-chlorobenzoyl)amino]ethyl}amino)carbonyl]phenyl}sulfonyl)(3-chlorophenyl)amino]acetate;
Benzyl4-(3-{[(2-tert-butoxy-2-oxoethyl)(3-chlorophenyl)amino]sulfonyl}benzoyl)piperazine-1-carboxylate;
tert-Butyl{(3-chlorophenyl)[(3-{[(3,3-diphenylpropyl)amino]carbonyl}phenyl)sulfonyl]amino}acetate;
Benzyl{2-[(3-{[(3-chlorophenyl)(2-{[(2,2-dimethyl-1,3-dioxolan-4-yl)methyl]amino}-2-oxoethyl)amino]sulfonyl}phenyl)amino]-2-oxoethyl}methylcarbamate;
benzyl(2-{[3-({(3-chlorophenyl) [2-(cyclohexylamino)-2-oxoethyl]amino}sulfonyl)phenyl]amino}-2-oxoethyl)methylcarbamate;
Benzyl(2-{[3-({(3-chlorophenyl)[2-oxo-2-(tetrahydro-2H-pyran-4-ylamino)ethyl]amino}sulfonyl)phenyl]amino}-2-oxoethyl)methylcarbamate;
Benzyl(2-{[3-({(3-chlorophenyl)[2-(isopropylamino)-2-oxoethyl]amino}sulfonyl)phenyl]amino}-2-oxoethyl)methylcarbamate;
Benzyl{2-[(3-{[(3-chlorophenyl)(2-{[2-(dimethylamino)ethyl]amino}-2-oxoethyl)amino]sulfonyl}phenyl)amino]-2-oxoethyl}methylcarbamate;
tert-Butyl[{[3-({[[(benzyloxy)carbonyl](methyl)amino]acetyl}amino)phenyl]sulfonyl}(4-chlorophenyl)amino]acetate;
tert-Butyl[{[3-({[[(benzyloxy)carbonyl](methyl)amino]acetyl}amino)phenyl]sulfonyl}(2-chlorophenyl)amino]acetate;
tert-Butyl[{[3-({[[(benzyloxy)carbonyl](methyl)amino]acetyl}amino)phenyl]sulfonyl}(phenyl)amino]acetate;
tert-Butyl[{[3-({[[(benzyloxy)carbonyl](methyl)amino]acetyl}amino)phenyl]sulfonyl}(3,5-dichlorophenyl)amino]acetate;
tert-Butyl{{[3-({[[(benzyloxy)carbonyl](methyl)amino]acetyl}amino)phenyl]sulfonyl}[3-(trifluoromethyl)phenyl]amino}acetate; and
tert-Butyl[{[3-({[[(benzyloxy)carbonyl](methyl)amino]acetyl}amino)phenyl]sulfonyl}(3-cyanophenyl)amino]acetate.

Methods of Preparation

The compounds of the present invention may be prepared by methods such as those illustrated in the following Schemes 1, 2 and 3. Solvents, temperatures, pressures, and other reaction conditions may be selected by one of ordinary skill in the art. Starting materials are commercially available or readily prepared by one of ordinary skill in the art.

Scheme 1 describes the preparation of the series where d=—N($R^4$)C(O)—. 3-Nitrobenzenesulfonyl chloride 1, optionally substituted with $R_a$, and aniline 2 are dissolved in a suitable solvent such as dichloromethane in the presence of a base such as triethylamine. The resulting sulfonamide 3 is dissolved in a suitable solvent such as dimethyl formamide and treated with an alkylating agent having the composition a-(b)$_n$-X, where X is a leaving group such as a halogen (Cl, Br or I), a tosyl group or a mesyl group and a base such as sodium hydride. The nitro group of the alkylated sulfonamide 4 is reduced using, for example, elemental iron in acetic acid and water. Other suitable reducing conditions may be employed such as tin(II) chloride or hydrogen with palladium on carbon. The aniline 5 is coupled with f-(e)$_m$-COY (6). When Y=chloride, aniline 5 and f-(e)$_m$-COY are together stirred in, for example, dichloromethane in the presence of a base such as triethylamine. When Y=hydroxyl, aniline 5 and 6 are stirred in, or example, dichloromethane, in the presence of a set of coupling reagents commonly employed for such reactions: 1-(3-dimethylaminopropyl)-3-ethylcarbodiimide hydrochloride, 1-hydroxy-7-azabenzotriazole and triethylamine. Other sets of reagents effecting the identical coupling may be employed are are well known to those skilled in the art. Both coupling protocols result in the formation of the final products 7. Thus, using the procedures described in synthetic scheme 1, examples 1-46 were produced.

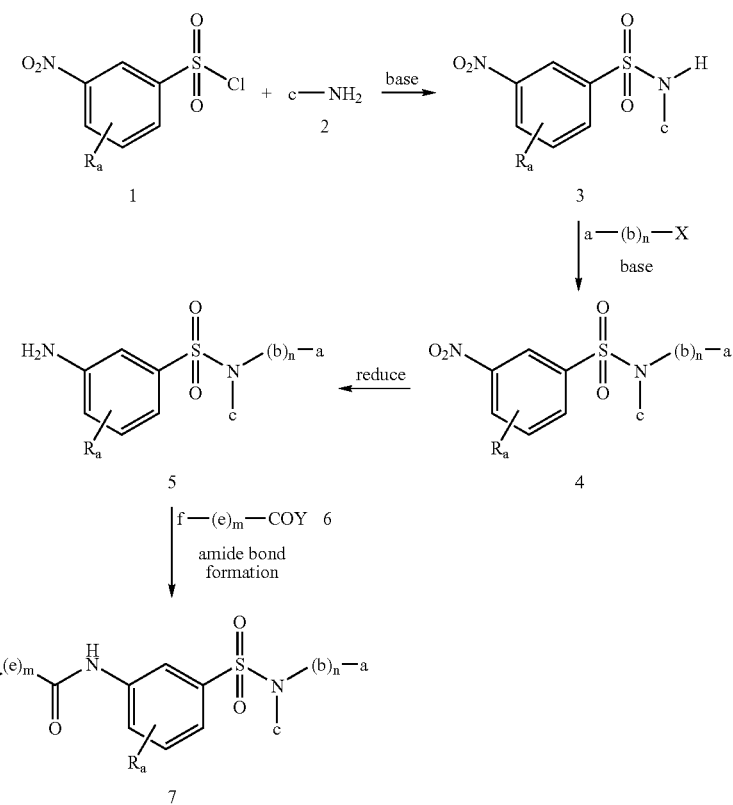

Scheme 2 describes the synthesis of the series where a=—C(O)NR²R³. Compound 7, where a=—C(O)OCH₂CH₃ is subjected to conditions whereby the ester functionality is hydrolyzed to the carboxylic acid or salt of the carboxylate anion. Examples of conditions effecting such a change include aqueous sodium hydroxide contained in a solvent such as methanol. The carboxylic acid or carboxylate salt thus formed is coupled with an amine under conditions described for such a reaction in Scheme 1. Using this two step sequence, examples 47-51 were prepared.

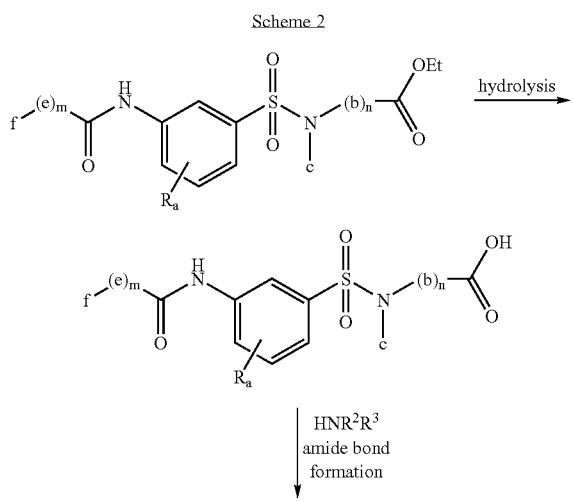

-continued

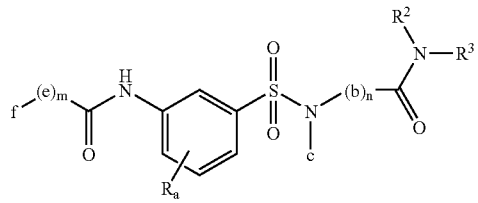

Scheme 3 describes the synthesis of the series where d=—C(O)N(R⁴)—. 3-Carboxybenzenesulfonyl chloride 8, optionally substituted with $R_a$, and aniline 2 are stirred in dichloromethane and treated with amberlite I120 (see PCT application WO02225999). The free acid 9 was esterified with, for example, refluxing methanolic hydrochloric acid. The 3-phenylsulfamoyl benzene benzoic acid methyl ester 10, optionally substituted with $R_a$, was alkylated a-(b)$_n$-X, where X is a halogen (Cl, Br or I), a tosyl group or a mesyl group, in the presence of a suitable base, for example, potassium carbonate, in a suitable solvent such as dimethyl formamide. The alkylated sulfonamide 11 was hydrolyzed to the acid 12 by the action of aqueous base, for example, lithium hydroxide in a combination of water and methanol. Amide bond formation between carboxylic acid 12 and amine 13 [f-(e)$_m$-NH₂] was accomplished using coupling reagents generally known to those skilled in the art: e.g., 1-(3-dimethylaminopropyl)-3-ethylcarbodiimide hydrochloride, 1-hydroxy-7-azabenzotriazole and triethylamine. Thus, by the procedures described in Scheme 3, examples 52-60 were synthesized.

Scheme 3

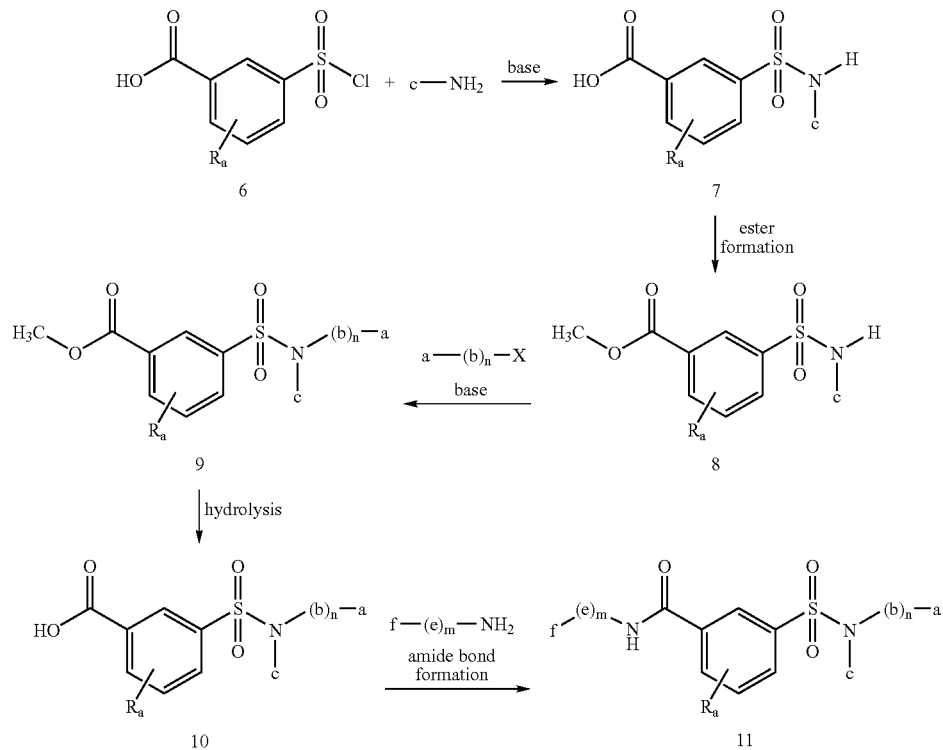

It is reason able to expect that the procedures described in Schemes 1, 2 and 3 may be extended using modifications known to those skilled in the art to include examples where d=—N(R$^4$)S(O)$_t$—, —S(O)$_t$N(R$^4$)— or —S(O)$_t$—.

Utility

The compounds of formula I and salts thereof are antagonists of calcium channels (especially T-type and/or L-type calcium channels) and are useful in treatment of calcium channel-dependent disorders. They are thus useful as antihypertensive agents. By the administration of a composition having one (or a combination) of the compounds of this invention, the blood pressure of a hypertensive mammalian (e.g., human) host is reduced. They are also useful in portal hypertension, hypertension secondary to treatment with erythropoietin and low renin hypertension.

The compounds of the present invention are also useful in the treatment of disorders related to renal, glomerular and mesangial cell function, including acute (such as ischemic, nephrotoxic, or glomerulonephritis) and chronic (such as diabetic, hypertensive or immune-mediated) renal failure, diabetic nephropathy, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention are also useful in the treatment of disorders related to paracrine and endocrine function. The compounds of this invention are also useful in the treatment of diabetic nephropathy, hypertension-induced nephropathy, and IGA-induced nephropathy.

The compounds of the present invention are also useful in the treatment of endotoxemia or endotoxin shock as well as hemorrhagic shock. The compounds of the present invention are also useful in alleviation of pain, including neuropathic pain, peripheral pain and pain associated with cancer, such as the pain associated with prostate cancer, and bone pain associated with bone cancer. The compounds of the present invention are further useful in the prevention and/or reduction of end-organ damage associated with cell-proliferation.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention are also useful as anti-arrhythmic agents; anti-anginal agents; anti-fibrillatory agents; anti-asthmatic agents; anti-atherosclerotic and anti-arteriosclerotic agents (including anti-transplantation arteriosclerotic agents); additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease, intermittent claudication and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer, inflammatory bowel disease and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedure including transplantation and stenting; therapy for congestive heart failure including inhibition of fibrosis; inhibition of left ventricular dilatation, remodeling and dysfunction; and treatment of hepatotoxicity and sudden death. The compounds of this invention are useful in the treatment of sickle cell disease including the initiation and/or evolution of the pain crises of this disease; treatment of the deleterious consequences of tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention are useful in therapy for metabolic and neurological disorders; cancer; insulin-dependent and non insulin-dependent diabetes mellitus; neuropathy; retinopathy; epilepsy; hemorrhagic and ischemic stroke; bone remodeling; psoriasis; and chronic inflammatory diseases such as arthritis, rheumatoid arthritis, osteoarthritis, sarcoidosis and eczematous dermatitis (all types of dermatitis).

The compounds of this invention are additionally useful in the treatment of disorders involving bronchoconstriction and disorders of chronic or acute pulmonary inflammation such as chronic obstructive pulmonary disease (COPD) and adult respiratory distress syndrome (ARDS).

The compounds of this invention are also useful in the treatment of sexual dysfunction in both men (erectile dysfunction, for example, due to diabetes mellitus, spinal cord injury, radical prostatectomy, psychogenic etiology or any other cause) and women by improving blood flow to the genitalia, especially, the corpus cavernosum.

The compounds of this invention are also useful in the treatment of dementia, including Alzheimer's dementia, senile dementia and vascular dementia.

Additionally the compounds of the present invention are further useful in the reduction of general morbidity and/or mortality as a result of the above utilities.

The present invention thus provides methods for the treatment of these disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

The effective amount of a compound of the present invention may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 5 to about 500 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to calcium channel-dependent disorders.

The present invention also provides pharmaceutical compositions comprising at least one of the compounds of the formula I capable of treating a calcium channel-dependent disorder in an amount effective therefor, and a pharmaceutically acceptable vehicle, carrier or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier. The compounds of formula I can also be formulated in compositions such as sterile solutions or suspensions for parenteral administration. About 0.1 to 500 milligrams of a compound of formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat peripheral vascular diseases and as such may be formulated as a cream or ointment.

The compounds of the present invention may be employed alone or in combination with each other and/or other suitable therapeutic agents. For example, the compounds of this invention can be formulated in combination with endothelin converting enzyme (ECE) inhibitors, such as phosphoramidon; thromboxane receptor antagonists such as ifetroban; potassium channel openers; thrombin inhibitors (e.g., hirudin and the like); growth factor inhibitors such as modulators of PDGF activity; platelet activating factor (PAF) antagonists; anti-platelet agents such as GPIIb/IIIa blockers (e.g., abciximab, eptifibatide, and tirofiban), P2Y(AC) antagonists (e.g., clopidogrel, ticlopidine and CS-747), and aspirin; anticoagulants such as warfarin, low molecular weight heparins such as enoxaparin, Factor VIIa inhibitors, and Factor Xa inhibitors such as those described in U.S. Ser. No. 09/496,571 filed Feb. 2, 2000 ; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; vasopepsidase inhibitors (dual NEP-ACE inhibitors) such as omapatrilat and gemopatrilat; HMG CoA reductase inhibitors such as pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates; bile acid sequestrants such as questran; niacin; anti-atherosclerotic agents such as ACAT inhibitors; MTP inhibitors such as those described in U.S. Ser. No. 09/007,938 filed Jan. 16, 1998 ; calcium channel blockers such as amlodipine besylate; potassium channel activators; alpha-adrenergic agents, beta-adrenergic agents such as carvedilol and metoprolol; antiarrhythmic agents, such as dofetilide, quinidine, ibutilide, propofanone, amiodarone; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; thrombolytic agents such as tissue plasminogen activator (tPA), recombinant tPA, streptokinase, urokinase, prourokinase and anisoylated plasminogen streptokinase activator complex (APSAC); anti-diabetic agents such as biguanides (e.g. metformin), glucosidase inhibitors (e.g., acarbose), insulins, meglitinides (e.g., repaglinide), sulfonylureas (e.g., glimepiride, glyburide, and glipizide), biguanide/glyburide combinations such as those described in U.S. Ser. No. 09/432,465 filed Nov. 3, 1999 and U.S. Ser. No. 09/460,920 filed Dec. 14, 1999 ; thiozolidinediones (e.g. troglitazone, rosiglitazone and pioglitazone), and PPAR-gamma agonists; mineralocorticoid receptor antagonists such as spironolactone and eplerenone; growth hormone secretagogues such as those described in U.S. Ser. No. 09/417,180 filed Oct. 12, 1999 and U.S. Ser. No. 09/506,749 filed Feb. 18, 2000 aP2 inhibitors such as those described in U.S. Ser. No. 09/391,053 filed Sep. 7, 1999 and U.S. Ser. No. 09/390,275 filed Sep. 7, 1999 digitalis; ouabian; non-steroidal antiinflammatory drugs (NSAIDS) such as aspirin and ibuprofen; phosphodiesterase inhibitors such as PDE III inhibitors (e.g., cilostazol) and PDE V inhibitors (e.g., sildenafil); protein tyrosine kinase inhibitors; antiinflammatories; antiproliferatives such as methotrexate, FK506 (tacrolimus, Prograf), mycophenolate and mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin); cyclosporins; steroids such as prednisone or dexamethasone; gold compounds; cytotoxic drugs such as azathiprine and cyclophosphamide; TNF-alpha inhibitors such as tenidap; anti-TNF antibodies or soluble TNF receptor such as etanercept (Enbrel) rapamycin (sirolimus or Rapamune), leflunimide (Arava); and cyclooxygenase-2 (COX-2) inhibitors such as celecoxib (Celebrex) and rofecoxib (Vioxx).

The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

If formulated as a fixed dose, such combination products employ the compounds of this invention within the dosage range described below and the other pharmaceutically active agent within its approved dosage range. The above other therapeutic agents, when employed in combination with the compounds of the present invention, may be used, for example, in those amounts indicated in the Physicians' Desk Reference (PDR) or as otherwise determined by one of ordinary skill in the art.

The following assays may be employed in ascertaining the degree of activity of a compound as an antagonists of calcium channels (especially T-type and/or L-type calcium channels). Compounds described in the following Examples have demonstrated measurable activity as calcium channel antagonists.

Aortic Ring Protocol:

Male Sprague-Dawley rats (250-300 g) were euthanized by $CO_2$ and cervical dislocation. The thoracic aorta was removed and placed in physiological salt solution (PSS) of the following composition, in mM: 118.4 NaCl, 4.7 KCl, 1.2 $MgCl_2$, 1.2 $KH_2PO_4$, 1.9 $CaCl_2$, 25.0 $NaHCO_3$, and 10.1 glucose. The aorta was cleaned of adherent connective tissue and cut into rings approximately 3 mm wide. The endothelium was removed from each ring by placing the ring on a dissecting probe and gently rolling on PSS-moistened filter paper. Each rat aortic ring was mounted for isometric force recording on stainless steel wires in a 10 ml organ chamber between a micrometer for control of tissue length and a GRASS® FT-03 force transducer. Mechanical responses were recorded using a PowerLab® data acquisition system. The organ chambers contained PSS aerated with 95% $O_2$, 5% $CO_2$ to maintain the pH at 7.4. The experiments were performed at 37° C. The tissues were gradually stretched over a 2 hr equilibration period to approximately 2 g preload. Compounds were tested for the ability to produce relaxation of aortic rings that were contracted with 80 mM KCl.

Patch-clamp Electropysiology:

T- and L-type calcium currents were studied using cell lines stably expressing the cloned human T-(alpha1H) and L-type calcium ion channel genes. Membrane current recordings were made with Axopatch 200A and 200B integrating patch-clamp amplifiers (Axon Instruments, Foster City, Calif.) using the whole-cell variant of the patch-clamp technique. The bath solution, which replaced the cell culture media during experiments, for T-type calcium current experiments contained (in mM): 140 NaCl, 5 $CaCl_2$, 4 KCl, 1 $MgCl_2$, 10 Glucose, 10 HEPES (pH 7.35, NaOH). The patch pipette filling solution used T-type calcium current experiments experiments contained (in mM): 130 KCl, 1 $CaCl_2$, 1 $MgCl_2$, 5 ATP-$K_2$, 10 EGTA, 10 HEPES (pH 7.2, KOH). The bath solution for L-type calcium current experiments contained (in mM): 103 NaCl, 30 $BaCl_2$, 4 CsCl, 1 $MgCl_2$, 10 glucose, 10 HEPES (pH 7.35, NaOH). The pipette solution used in L-type calcium current experiments contained (in mM): 20 CsCl, 20 tetraethylammonium chloride, 82 glutamate, 3 ATP-Mg, 0.5 $NaH_2PO_4$, 3 $Na_2$-creatine $PO_4$, 11 EGTA, 10 HEPES (pH 7.25, CsOH). The bath and pipette solutions used in L-type calcium current studies minimized current "rundown" over time. Barium has a greater conductance than calcium through the L-type calcium channel and was used as charge carrier in L-type calcium channel experiments to increase whole-cell current amplitude. No protein was present in bath solutions, so concentrations of test agents represent free or unbound test agent.

T-type calcium currents were elicited by repetitive 200 ms voltage steps to −30 mV applied from a holding potential of −80 mV. The repetitive voltage steps were continuously applied at a frequency of 0.2 Hz throughout experiments. Effects of compounds were calculated by measuring inhibition of peak current elicited during voltage steps. Peak current was measured from the holding current at −80 mV and used to calculate per cent inhibition. L-type calcium currents were elicited by repetitive 200 ms voltage steps to 30 mV applied from a holding potential of −50 mV. The repetitive voltage steps were continuously applied at a frequency of 0.2 Hz throughout experiments. Effects of compounds were calculated by measuring inhibition of peak current recorded at 30 mV. Data were sampled at rates at least two times the low pass filter rate. The flow rate was kept constant throughout the experiments (~5 ml/min). All membrane currents were recorded at 25°C.

The following Examples illustrate embodiments of the present invention, and are not intended to limit the scope of the claims. Abbreviations employed herein are defined below.

Abbreviations $CH_3CN$=acetonitrile
DCC=dicyclohexylcarbodiimide
DCE=dichloroethane
DCM=dichloromethane
DMAP=4-dimethylaminopyridine
DIPEA or DIEA=N,N-diisopropylethylamine
DME=1,2-dimethoxyethane
DMF=dimethyl formamide
EDCI=1-3-dimethylaminopropyl)-3-ethylcarbodiimide
$Et_2O$=diethyl ether
HOBT=1-hydroxybenzotriazole
EtOAc=ethyl acetate
HCl=hydrochloric acid
KOH=potassium hydroxide
$K_2CO_3$=potassium carbonate
$LiAlH_4$=lithium aluminum hydride
MeCN=acetonitrile
MeOH=methanol
$MgSO_4$=magnesium sulfate
NaH=sodium hydride
NaOH=sodium hydroxide
NMP=1-methyl-2-pyrrolidinone
$SOCl_2$=thionyl chloride
TEA=triethylamine
THF=tetrahydrofurane
bp=boiling point
g=gram(s)
mg=milligram(s)
ml=milliliter
μl=microliter
l=liter
mmol=millimole
μmol=micromole
mol=mole
mp=melting point
RT=room temperature
NMR (Nuclear Magnetic resonnance was performed on a Brucker 200 spectrometer (s=singulet, d=doublet, t=triplet, dd=doublet of doublet, m=multiplet) Elementary analysis were carried on a Carlo-Erba Mod 106 elementary analyzer

EXAMPLES

The following Examples illustrate embodiments of the present invention, and are not intended to limit the scope of the claims.

Compounds of the Examples are identified by the example and step in which they are prepared (for example, "1A" denotes the title compound of step A of Example 1), or by the example only where the compound is the title compound of the example (for example, "4" denotes the title compound of Example 4).

Example 1

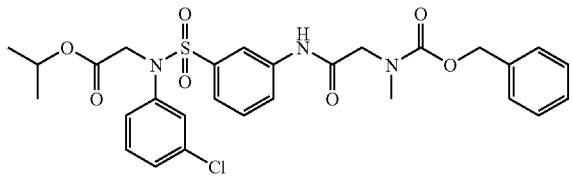

N-(3-chlorophenyl)-N-[[3-[[[methyl[(phenyl-methoxy)carbonyl]amino]acetyl]-amino]phenyl]sulfonyl]-glycine, 1-methylethyl ester

1A

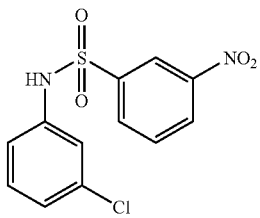

3-Nitrobenzene sulfonyl chloride (5.76 g, 26 mmol) was dissolved in dichloromethane (100 mL) under a blanket of argon. Triethyl amine was added to the flask followed by 3-chloroaniline (2.4 g, 19 mmol) in dichloromethane (15 mL). The reaction was stirred at rt for 12 h. The reaction was washed with 1 N aqueous HCl (2×100 mL) and saturated aqueous sodium chloride (2×100 mL), dried over anhyd sodium sulfate and dried in vacuo. Compound 1A was isolated as a yellow solid (4.5 g, 76% yield) and was used in the next step without futher purification.

1B

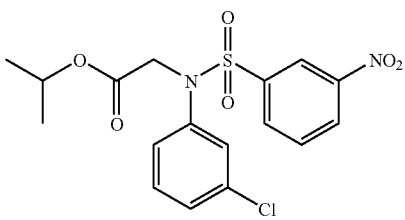

Compound 1A (4.43 g, 14.2 mmol) was placed in a round bottomed flask. The flask was evacuated and back-filled with argon. 1A was dissolved in dimethylformamide (35 mL) and treated with sodium hydride (60% oil dispersion; 681 mg, 17.0 mmol). The reaction mixture was stirred for 30 min at rt. Isopropyl bromoacetate (3.60 g, 19.9 mmol, 2.6 mL) was added dropwise over 15 min. The reaction was stirred at rt for 12 h. The reaction was diluted with ethyl acetate and washed with water (2×100 mL) and saturated aqueous sodium chloride (100 mL). The organic layer was dried over anhyd magnesium sulfate, filtered and dried in vacuo. The compound was purified by silica gel chromatography to yield 1.9 g (32%) of compound 1B. $^1$H-NMR (400 MHz; CDCl$_3$) δ 1.23 (d, 6 H, J=6.15 Hz), 5.01 (heptet, 1 H, J=6.15 Hz), 7.16 (bd, 1 H, J=7.91 Hz), 7.26-7.29 (m, 2 H), 7.34 (m, 1 H), 7.68 (t, 1 H, J=8.13 Hz), 7.98 (bd, 1 H, J=7.47 Hz), 8.44 (m, 1 H), 8.56 (m, 1 H); mass spec m/z=430.0 (M+NH$_4^+$)$^+$.

1C

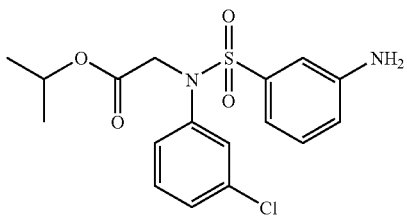

Compound 1B (850 mg, 2.1 mmol) was dissolved in glacial acetic acid (5.0 mL) and water (0.5 mL) and treated with iron powder (38 mg, 6.8 mmol). The reaction was stirred vigorously and was complete after 4 h. The reaction was diluted with ethyl acetate, washed with saturated aqueous sodium bicarbonate and brine, dried over magnesium sulfate, filtered and dried in vacuo yielding 800 mg (>99%) of compound 1C, which was carried onto the next step without further purification.

Mass spec m/z=383.0 (M+H)$^+$.

Example 1

Compound 1C (50 mg, 0.13 mmol), N-(benzyloxy-carbonyl)sarcosine (44 mg, 0.20 mmol) and 1-hydroxy-7-azabenzotriazole (50 mg, 0.37 mmol) were dissolved in dichloromethane (0.8 mL). N-methylmorpholine (46 mg, 0.45 mmol, 50 uL) was added followed by 1-(3-dimethylaminopropyl)-3-ethylcarbodiimide hydrochloride (50 mg, 0.26 mmol). The reaction was stirred at rt for 12 h. The entire reaction was placed on a pre-packed silica gel column (4 g SiO2) and the column eluted with with a gradient consisting of 0 to 100% ethyl acetate in hexane to provide Example 1 (28.9 mg, 38% yield). $^1$H-NMR (400 MHz; CDCl$_3$) δ 1.19 (d, 1 H, J=6.59 Hz), 3.09 (s, 3 H), 4.05 (s, 2 H), 4.36 (s, 2 H), 5.01 (m, 1 H), 7.13 (m, 1 H), 7.24-7.43 (m, 9 H), 7.79 (m, 2 H), 8.39 (bs, 1 H); mass spec m/z=585.9 (M–H)$^-$.

Example 2

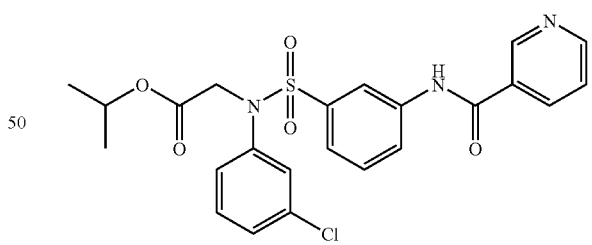

N-[3-[2-(Pyridin-3-yl-carbonyl-amino)-acetylamino]-benzenesulfonyl]-N-(3-chlorophenyl) glycine isopropyl ester Example 2 was produced in by treating compound IC (50 mg, 0.13 mmol) with triethyl amine (82 mg, 0.81 mmol, 60 uL) and nicotinyl chloride (46 mg, 0.26 mmol) in dichloromethane (0.4 mL). Mass spec m/z=485.0 (M–H)$^-$.

The following compounds in Tables 1-4 were synthsized utilizing the appropriate proceedure as described for Example 1 or Example 2.

TABLE 1

| Compound number | —d—(e)ₘ—f | Mass spec (m/z) | HPLC purity (%) |
|---|---|---|---|
| 3 | (3-phenoxybenzamide linker) | 576.9 (M − H)⁻ | 92 |
| 4 | (3,3-diphenylpropanamide linker) | 589.0 (M − H)⁻ | 92 |
| 5 | (acetamide linker) | 423.0 (M − H)⁻ | 93 |
| 6 | (N-Fmoc-piperidine-4-carboxamide linker) | 714.0 (M − H)⁻ | 85 |
| 7 | (N-Cbz-prolinamide linker) | 612.0 (M − H)⁻ | 87 |
| 8 | (N-Cbz-prolinamide linker) | 612.0 (M − H)⁻ | 97 |
| 9 | (N-Cbz-glycinamide linker) | 595.9 (M + Na⁺)⁺ | 99 |

TABLE 1-continued

| Compound number | —d—(e)$_m$—f | Mass spec (m/z) | HPLC purity (%) |
|---|---|---|---|
| 10 | | 616.0 (M − H)$^-$ | 97 |
| 11 | | 586.0 (M − H)$^-$ | 95 |
| 12 | | 654.0 (M − H)$^-$ | 85 |
| 13 | | 556.0 (M − H)$^-$ | 89 |
| 14 | | 499.0 (M − H)$^-$ | 96 |
| 15 | | 513.0 (M − H)$^-$ | 96 |
| 16 | | 527.3 (M − H)$^-$ | 95 |
| 17 | | 557.0 (M − H)$^-$ | 97 |

TABLE 1-continued

| Compound number | —d—(e)$_m$—f | Mass spec (m/z) | HPLC purity (%) |
|---|---|---|---|
| 18 | | 619.0 (M + NH$_4^+$)$^+$ | 98 |
| 19 | | 557.0 (M − H)$^-$ | 97 |
| 20 | | 549.0 (M − H)$^-$ | 90 |
| 21 | | 538.0 (M − H)$^-$ | 88 |
| 22 | | 552.2 (M − H)$^-$ | 97 |
| 23 | | 711.0 (M + NH$_4^+$)$^+$ | 99 |
| 24 | | 549.0 (M − H)$^-$ | 97 |

TABLE 1-continued

| Compound number | —d—(e)ₘ—f | Mass spec (m/z) | HPLC purity (%) |
|---|---|---|---|
| 25 | | 549.0 (M − H)⁻ | 90 |
| 26 | | 571.1 (M − H)⁻ | 98 |
| 27 | | 528.9 (M + NH₄⁺)⁺ | 99 |

TABLE 2

| Compound number | —(e)ₘ—f | Mass spec (m/z) | HPLC purity (%) |
|---|---|---|---|
| 28 | | 600.2 (M − H)⁻ | 99 |
| 29 | | 614.0 (M − H)⁻ | 99 |

TABLE 2-continued

| Compound number | —(e)ₘ—f | Mass spec (m/z) | HPLC purity (%) |
|---|---|---|---|
| 30 | | 614.0 (M − H)⁻ | 90 |
| 31 | | 614.0 (M − H)⁻ | 90 |
| 32 | | 466.0 (M − H)⁻ | 99 |
| 33 | | 707.3 (M + NH₄⁺)⁺ | 92 |

TABLE 3

| Compound number | R¹—(b)ₙ— | Mass spec (m/z) | HPLC purity (%) |
|---|---|---|---|
| 34 | | 633.3 (M − H)⁻ | 87 |
| 35 | | 575.9 (M − H)⁻ | 94 |
| 36 | | 569.9 (M − H)⁻ | 91 |
| 37 | | 544.0 (M − H)⁻ | 91 |
| 38 | | 599.9 (M − H)⁻ | 99 |

TABLE 3-continued

[Structure: R¹—(b)ₙ—N(3-chlorophenyl)—SO₂—(3-aminophenyl)—NH—C(O)—CH₂—N(CH₃)—C(O)—O—CH₂—phenyl]

| Compound number | R¹—(b)ₙ— | Mass spec (m/z) | HPLC purity (%) |
|---|---|---|---|
| 39 | ethyl —CH₂—C(O)—O—ethyl | 557.9 (M − H)⁻ | 99 |
| 40 | H₃C—O—C(O)—CH₂— | 571.9 (M − H)⁻ | 99 |

TABLE 4

[Structure: tBuO—C(O)—CH₂—N(c)—SO₂—(3-aminophenyl)—NH—C(O)—CH₂—N(CH₃)—C(O)—O—CH₂—phenyl]

| Compound number | c | Mass spec (m/z) | HPLC purity (%) |
|---|---|---|---|
| 41 | 4-chlorophenyl | 619.2 (M + NH₄⁺)⁺ | 99 |
| 42 | 2-chlorophenyl | 619.2 (M + NH₄⁺)⁺ | 99 |
| 43 | phenyl | 585.2 (M + NH₄⁺)⁺ | 95 |
| 44 | 3,5-dichlorophenyl | 653.2 (M + NH₄⁺)⁺ | 91 |

TABLE 4-continued

| Compound number | c | Mass spec (m/z) | HPLC purity (%) |
|---|---|---|---|
| 45 | 3-trifluoromethylphenyl | 631.1 (M − H)⁻ | 97 |
| 46 | 3-cyanophenyl | 610.2 (M + NH₄⁺)⁺ | 93 |

Example 47

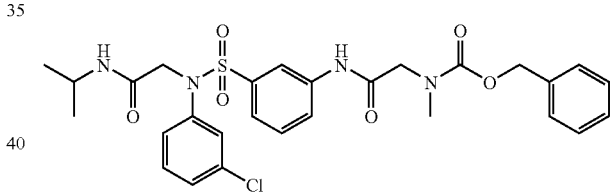

Compound 37 (55 mg, 0.10 mmol), isopropylamide (9 mg, 0.10 mmol, 13 uL) and 1-hydroxy-7-azabenzotriazole (21 mg, 0.15 mmol) were dissolved in a 1:1 mixture of dimethylformamide and dichloromethane (1.0 mL). N-methylmorpholine (31 mg, 0.30 mmol, 33 uL) was added followed by 1-(3-dimethylaminopropyl)-3-ethylcarbodiimide hydrochloride (29 mg, 0.15 mmol). The reaction was stirred at rt for 12 h. The entire reaction was placed on a pre-packed silica gel column (4 g SiO₂) and the column was eluted with with a gradient consisting of 0 to 100% ethyl acetate in hexane to provide Example 47 (19.3 mg, 33% yield).

¹H-NMR (500 MHz, d4-MeOH) δ 1.03 (d, 6 H, J=6.60 Hz), 3.05 (app d, 3 H, 3.85 Hz), 3.87 (heptet, 1 H, J=6.60 Hz), 4.11 (app d, 2 H, J=12.1 Hz), 4.24 (s, 2 H), 5.10 (s, 1 H), 5.16 (s, 1 H), 7.06 (bd, 1 H, J=7.70 Hz), 7.22-7.41 (m, 9 H), 7.48 (t, 1 H, J=8.25 Hz), 7.76 (bd, 0.5 H, J=8.25 Hz), 7.82 (bd, 0.5 H, J=8.25 Hz), 7.97 (t, 2 H, J=14.8 Hz); mass spec m/z=585.3 (M−H)⁻, 604.4 (M+NH₄⁺)⁺.

The following compounds in Table 5 were synthsized utilizing the procedure as described for Example 47.

TABLE 5

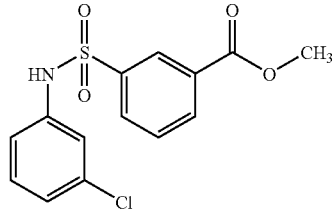

| Compound number | R¹—(b)ₙ— | Mass spec (m/z) | HPLC purity (%) |
|---|---|---|---|
| 48 | | 657.3 (M − H)⁻ | 95 |
| 49 | | 625.3 (M − H)⁻ | 90 |
| 50 | | 627.3 (M − H)⁻ | 94 |
| 51 | | 614.4 (M − H)⁻<br>616.4 (M + H)⁺ | 99 |

Example 52

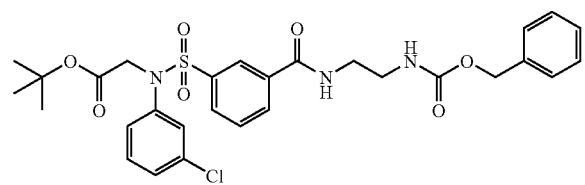

N-(3-chlorophenyl)-N-[[3-[[[2-[[(phenylmethoxy)-carbonyl]amino]ethyl]-amino]carbonyl]phenyl]sulfonyl]-glycine, 1,1-dimethylethyl ester

52A

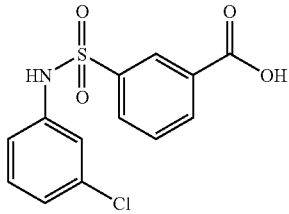

3-Chloroaniline (1.45 g, 11.3 mmol) was dissolved in dichloromethane (36 mL) and treated with 3-(chlorosulfonyl)-benzoic acid (1.0 g, 4.5 mmol). The reaction was stirred for 18 h at rt. The solvent was removed in vacuo, the residue was redissolved in methanol and stirred with Amberlite I120 for 3 h. The resin was filtered off and the solvent evaporated in vacuo to yield compound 52A (70% yield). The crude product was carried onto the next reaction without further purification.

52B

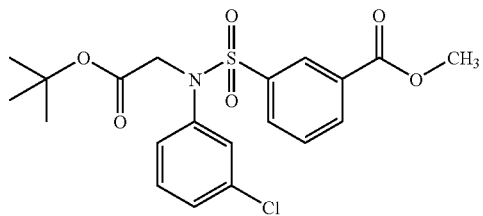

Compound 52A (500 mg, 1.53 mmol) was refluxed in saturated methanolic hydrochloric acid (30 mL) for 12 h. The solvent was removed in vacuo and the crude product passed through a plug of silica gel to provide compound 52B (80% yield).

¹H-NMR (500 MHz; CDCl₃) δ 3.94 (s, 3 H), 6.71 (bs, 1 H), 6.97 (d, 1 H, J=7.1 Hz), 7.11 (d, 1 H, J=6.6 Hz), 7.18 (t, 1 H, J=7.0 Hz), 7.57 (t, 1 H, J=8.0 Hz), 7.95 (d, 1 H, J=8.2 Hz), 8.24 (d, 1 H, J=8.2 Hz), 8.49 (s, 1 H).

52C

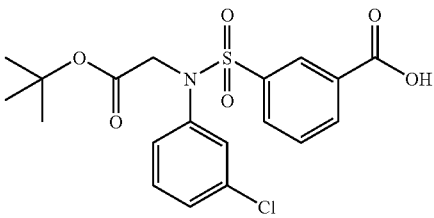

Compound 52B (150 mg, 0.46 mmol) was dissolved in anhyd dimethyl formamide (1.15 mL). Potassium carbonate (169 mg, 1.2 mmol) was added the solution and the reaction stirred for 10 min before t-butyl bromoacetate (132 mg, 0.68 mmol) was added dropwise. The reaction stirred at rt for 12 h. The reaction was diluted with ethyl acetate, washed with water and saturated aqueous sodium chloride, dried over anyd sodium sulfate, filtered and dried in vacuo. Compound 52C (205 mg, >99% yield) was isolated by silica gel chromatography. ¹H-NMR (500 MHz; CDCl₃) δ 1.40 (s, 9 H), 3.94 (s, 3H), 4.31 (s, 2 H), 7.12 (d, 1 H, J=7.7 Hz), 7.23-7.24 (m, 2 H), 7.29 (d, 1 H, J=8.2 Hz), 7.56 (t, 1 H, J=8.0 Hz), 7.82 (d, 1 H, J=7.7 Hz), 8.26 (d, 1 H, J=7.7 Hz), 8.35 (s, 1 H).

52D

Compound 52C (50 mg, 0.114 mmol) was dissolved in tetrahydrofuran (0.6 mL) and treated with 0.02 M aqueous lithium hydroxide (0.1 mL) and stirred at rt for 2 h. The reaction was diluted with pH 4.0 buffer and extracted with ethyl acetate. The combined organic extracts were were washed with saturated aqueous sodium chloride , dried over magnesium sulfate and evaporated to dryness to yield compound 52D (50 mg, >99%). ¹H-NMR (500 MHz; CDCl₃) δ

1.40 (s, 9 H), 4.38 (s, 2 H), 7.12 (d, 1 H, J=7.7 Hz), 7.28-7.34 (m, 3 H), 7.66 (t, 1 H, J=7.7 Hz), 7.86 (d, 1 H, J=7.7 Hz), 8.22 (s, 1 H), 8.27 (d, 1 H, J=7.7 Hz); mass spec m/z=423.9 (M−H)⁻.

Example 52

Compound 52D (40 mg, 0.093 mmol), N-hydroxy-7-azabenzotriazole (28 mg, 0.20 mmol), and N-(Benzyloxy-carbonyl)-1,2-diaminoethane (31 mg, 0.16 mmol) and 4-methylmorpholine (37 mg, 0.36 mmol) were dissolved in dichloromethane (0.4 mL). 1-(3-Dimethylaminopropyl)-3-ethylcarbodiimide hydrochloride (38 mg, 0.20 mmol) was added to the flask and the reaction was stirred for 12 h. Example 52 was isolated by silica gel chromatography (ethyl acetate/hexanes) yielding 29 mg (52% yield). Mass spec m/z=602.1(M+H)⁺.

The following compounds in Table 6 were synthsized utilizing the proceedures described for Example 52.

TABLE 6

| Compound number | —d—(e)ₘ—f | Mass spec (m/z) | HPLC purity (%) |
|---|---|---|---|
| 53 | | 584.2 (M − H)⁻ | 98 |
| 54 | | 598.0 (M − H)⁻ | 99 |
| 55 | | 618.0 (M + H)⁺ | 95 |
| 56 | | 612.1 (M + H)⁺ | 95 |
| 57 | | 583.1 (M + H)⁺ | 95 |
| 58 | | 645.1 (M + NH₄⁺)⁺ | 99 |
| 59 | | 619.2 (M + H)⁺ | 97 |

TABLE 6-continued

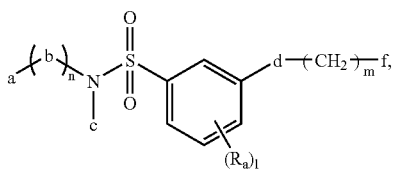

| Compound number | —d—(e)$_m$—f | Mass spec (m/z) | HPLC purity (%) |
|---|---|---|---|
| 60 | 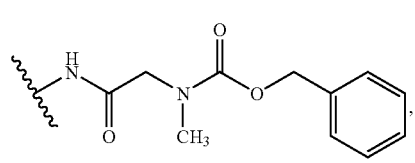 | 604.0 (M − H)$^-$ | 99 |

What is claimed is:

1. A compound of the formula I,

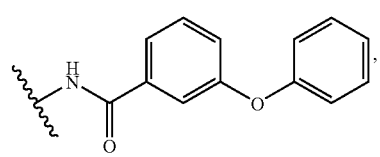

its stereoisomers, solvates, and salts, thereof, wherein:

a is R$^1$, >C$_3$alkyl, substituted alkyl, cycloalkyl or aryl;

R$^1$ is —C(O)NR$^2$R$^3$ or C(O)OR$^4$—;

R$^2$ and R$^3$ are independently
  (a) hydrogen;
  (b) alkyl, substituted alkyl, cycloalkyl, aryl, (aryl)alkyl, or (cycloalkyl)alkyl, b is CR$^{13}$R$^{14}$;

c is aryl;

R$^4$ is hydrogen, alkyl, substituted alkyl, cycloalkyl, aryl, (aryl)alkyl or (cycloalkyl)alkyl;

-d-(CH$_2$)$_m$-f is selected from

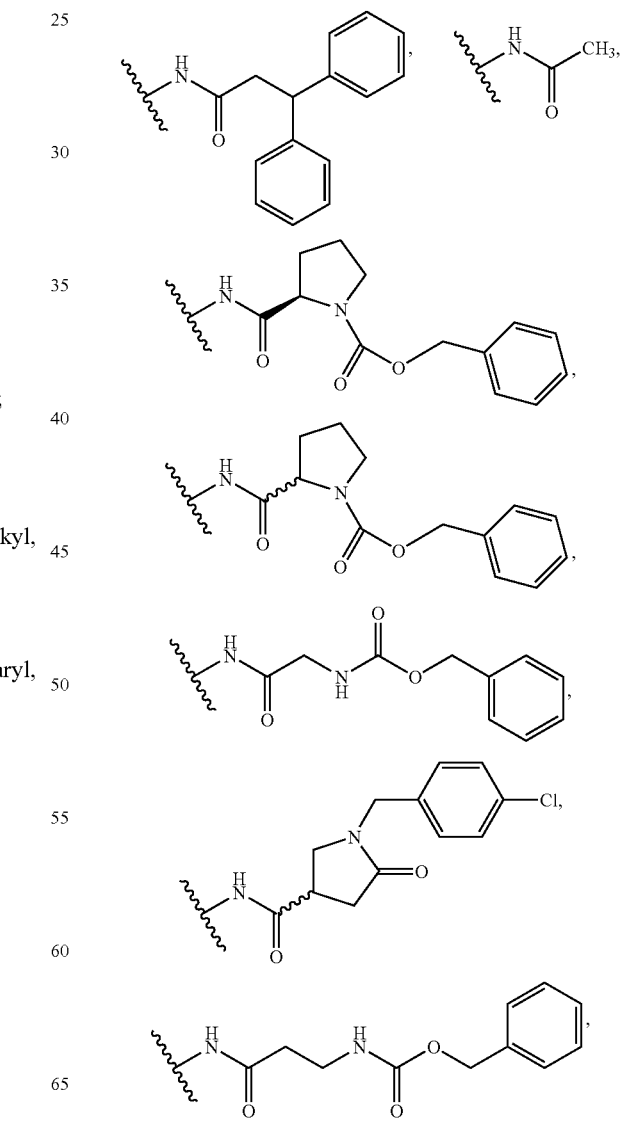

-continued
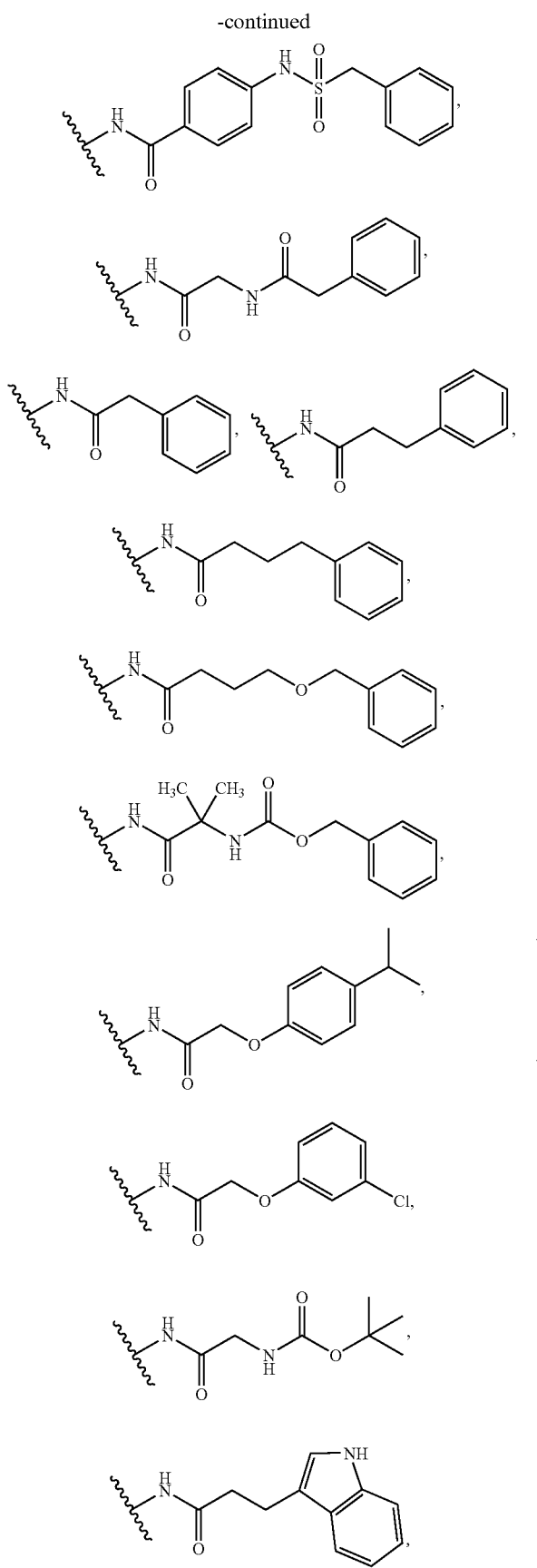
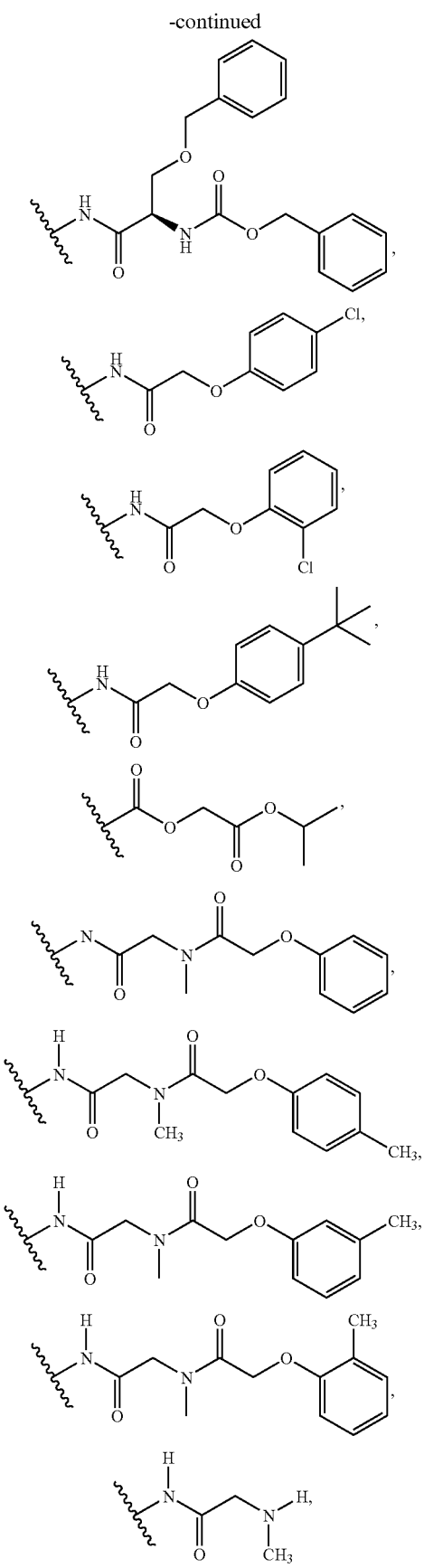

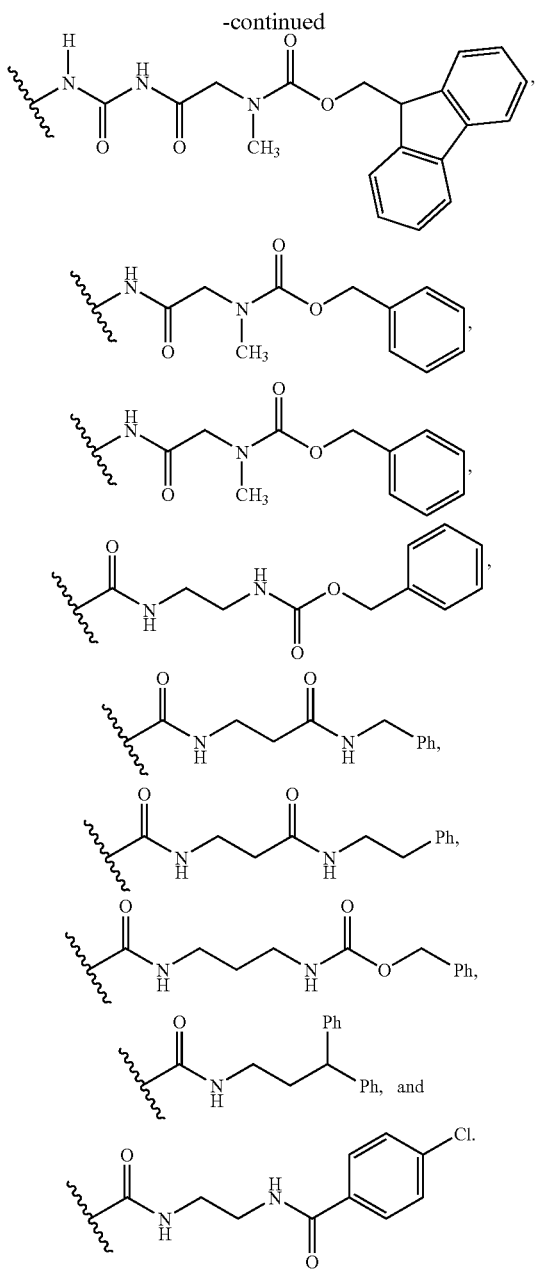

l, m, and n are independently 0 to 4;

$R_a$, $R^{13}$ and $R^{14}$ are independently hydrogen, cyano, nitro, halogen, alkyl, substituted alkyl, aryl, cycloalkyl, —$OR^{15}$, —$SR^{15}$, —$OC(=O)R^{15}$, —$C(=O)R^{15}$, —$CO_2R^{15}$, —$C(=O)NR^{16}R^{17}$, —$NR^{16}R^{17}$, —$S(=O)R^{15}$; or —$SO_2R^{15}$;

or $R^{13}$ and $R^{14}$ are taken together to form oxo;

$R^{15}$, $R^{16}$ and $R^{17}$ are independently hydrogen, alkyl, substituted alkyl, cycloalkyl, aryl, (aryl)alkyl, or (cycloalkyl)alkyl,; and $R^{21}$ and $R^{22}$ are independently hydrogen or $C_{1-4}$alkyl;

provided that:
when c is phenyl and $R_a$ is located para to the sulfoxide substituent; $R_a$ is not chloro or —OMe; and
when a is >$C_3$ alkyl, n is 0.

2. A compound of claim 1, its stereoisomers, solvates and salts, thereof, wherein:
a is $C_{4-8}$alkyl, aryl, or $R^1$; and
$R^{13}$ and $R^{14}$ are independently hydrogen or $C_{1-4}$alkyl.

3. A compound of claim 1, having the structure

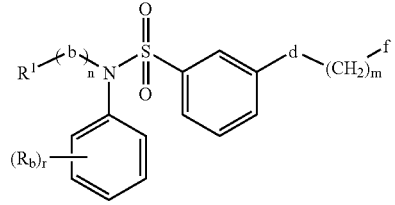

its stereoisomers, solvates, and salts, thereof, wherein:
$R_b$, is hydrogen, cyano, nitro, halogen, alkyl, substituted alkyl, aryl, cycloalkyl, —$OR^{18}$, —$SR^{18}$, —$OC(=O)R^{18}$, —$C(=O)R^{18}$, —$CO_2R^{18}$, —$C(=O)NR^{19}R^{20}$, —$NR^{19}R^{20}$, —$S(=O)R^{18}$, or —$SO_2R^{18}$;
$R^{18}$, $R^{19}$ and $R^{20}$ are independently hydrogen; alkyl, substituted alkyl, cycloalkyl, aryl, (aryl)alkyl, or (cycloalkyl)alkyl;
r is 0, 1, 2 or 3; and
$R^{13}$ and $R^{14}$ are independently hydrogen or $CH_3$.

4. A compound of claim 1 having the structure:

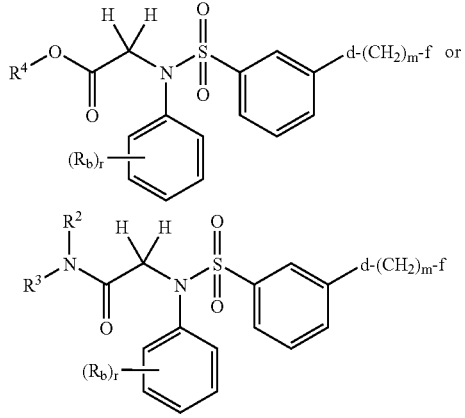

their stereoisomers, solvates, and salts, thereof, wherein:
$R^2$ is hydrogen or $C_{1-4}$alkyl;
$R^3$ is alkyl, cycloalkyl, (cycloalkyl)alkyl, or aminoalkyl; and
$R^4$ is selected from hydrogen; alkyl, cycloalkyl, (aryl)alkyl, (cycloalkyl)alkyl.

5. A compound of claim 1, its stereoisomers, solvates, and salts, thereof, wherein -a-(b)$_n$- is selected from:

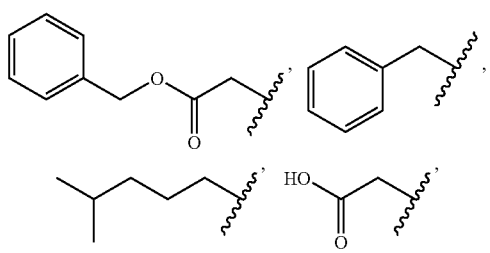

-continued

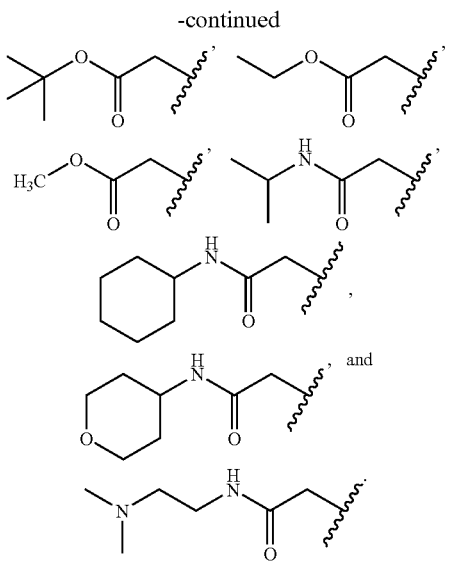

6. A compound of claim 1, its stereoisomers, solvates, and salts, thereof, wherein:
c is selected from:

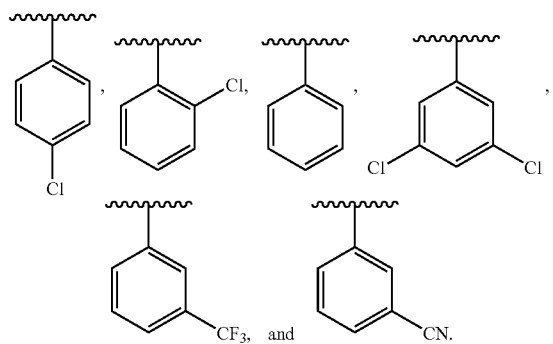

7. A compound of claim 1, its stereoisomers, solvates, and salts, thereof, selected from the following:
Isopropyl{(3-chlorophenyl)[(3-nitrophenyl)sulfonyl]amino}acetate;
Isopropyl[[(3-aminophenyl)sulfonyl](3-chlorophenyl)amino]acetate;
Isopropyl[(3-chlorophenyl)({3-[(3-phenoxybenzoyl)amino]phenyl}sulfonyl)amino]acetate;
Isopropyl[(3-chlorophenyl)({3-[(3,3-diphenylpropanoyl)amino]phenyl}sulfonyl)amino]acetate;
Isopropyl[{[3-(acetylamino)phenyl]sulfonyl}(3-chlorophenyl)amino]acetate;
Benzyl (2R)-2-[[(3-{[(3-chlorophenyl)(2-isopropoxy-2-oxoethyl)amino]sulfonyl}phenyl)amino]carbonyl}pyrrolidine-1-carboxylate;
Benzyl (2S)-2-[[(3-{[(3-chlorophenyl)(2-isopropoxy-2-oxoethyl)amino]sulfonyl}phenyl)amino]carbonyl}pyrrolidine-1-carboxylate;
Isopropyl[{[3-({[[(benzyloxy)carbonyl](methyl)amino]acetyl}amino)phenyl]sulfonyl}(3-chlorophenyl)amino]acetate;
Isopropyl[({3-[({[(benzyloxy)carbonyl]amino}acetyl)amino]phenyl}sulfonyl)(3-chlorophenyl)amino]acetate;
Isopropyl{{[3-({[1-(4-chlorobenzyl)-5-oxopyrrolidin-3-yl]carbonyl}amino)phenyl]sulfonyl}(3-chlorophenyl)amino]acetate;
Isopropyl[({3-[(3-{[(benzyloxy)carbonyl]amino}propanoyl)amino]phenyl}sulfonyl)(3-chlorophenyl)amino]acetate;
Isopropyl[{[3-({4-[(benzylsulfonyl)amino]benzoyl}amino)phenyl]sulfonyl}(3-chlorophenyl)amino]acetate;
Isopropyl ((3-chlorophenyl){[3-({[(phenylacetyl)amino]acetyl}amino)phenyl]sulfonyl}amino)acetate;
Isopropyl[(3-chlorophenyl)({3-[(phenylacetyl)amino]phenyl}sulfonyl)amino]acetate;
Isopropyl[(3-chlorophenyl)({3-[(3-phenylpropanoyl)amino]phenyl}sulfonyl)amino]acetate;
Isopropyl[(3-chlorophenyl)({3-[(4-phenylbutanoyl)amino]phenyl}sulfonyl)amino]acetate;
Isopropyl[[(3-{[4-(benzyloxy)butanoyl]amino}phenyl)sulfonyl](3-chlorophenyl)amnino]acetate;
Isopropyl[({3-[(2-{[(benzyloxy)carbonyl]amino}-2-methylpropanoyl)amino]phenyl}sulfonyl)(3-chlorophenyl)amino]acetate;
Isopropyl{(3-chlorophenyl)[(3-{[(4-isopropylphenoxy)acetyl]amino}phenyl)sulfonyl]amino}acetate;
Isopropyl[[(3-{[(3-chlorophenoxy)acetyl]amino}phenyl)sulfonyl](3-chlorophenyl)amino]acetate;
Isopropyl[{[3-({[(tert-butoxycarbonyl)amino]acetyl}amino)phenyl]sulfonyl}(3-chlorophenyl)amino]acetate;
Isopropyl{(3-chlorophenyl)[(3-{[3-(1H-indol-3-yl)propanoyl]amino}phenyl)sulfonyl]amino}acetate;
Isopropyl[({3-[((2R)-3-(benzyloxy)-2-{[(benzyloxy)carbonyl]amino}propanoyl)amino]phenyl}sulfonyl)(3-chlorophenyl)amino]acetate;
Isopropyl[[(3-{[(4-chlorophenoxy)acetyl]amino}phenyl)sulfonyl](3-chlorophenyl)amino]acetate;
Isopropyl[[(3-{[(2-chlorophenoxy)acetyl]amino}phenyl)sulfonyl](3-chlorophenyl)amino]acetate;
Isopropyl[[(3-{[(4-tert-butylphenoxy)acetyl]amino}phenyl)sulfonyl](3-chlorophenyl)amino]acetate;
2-Isopropoxy-2-oxoethyl 3-{[(3-chlorophenyl)(2-isopropoxy-2-oxoethyl)amino]sulfonyl}benzoate;
Methyl[{[3-({[[(benzyloxy)carbonyl](methyl)amino]acetyl}amino)phenyl]sulfonyl}(3-chlorophenyl)amino]acetate;
Ethyl[{[3-({[[(benzyloxy)carbonyl](methyl)amnino]acetyl}amino)phenyl]sulfonyl}(3-chlorophenyl)amino]acetate;
tert-Butyl[{[3-({[[(benzyloxy)carbonyl](methyl)amino]acetyl}amino)phenyl]sulfonyl}(3-chlorophenyl)amino]acetate;
Benzyl[{[3-({[[(benzyloxy)carbonyl](methyl)amino]acetyl}amino)phenyl]sulfonyl}(3-Benzyl{2-[(3-{[benzyl(3-chlorophenyl)amino]sulfonyl}phenyl)amnino]-2-oxoethyl}methylcarbamate;
Benzyl{2-[(3-{[(3-chlorophenyl)(4-methylpentyl)amino]sulfonyl}phenyl)amino]-2-oxoethyl}methylcarbamate;
[{[3-({[[(Benzyloxy)carbonyl](methyl)amino]acetyl}amino)phenyl]sulfonyl}(3-chlorophenyl)amino]acetic acid;
tert-Butyl ((3-chlorophenyl){[3-({[methyl(phenoxyacetyl)amino]acetyl}amino)phenyl]sulfonyl}amino)acetate;
tert-Butyl[(3-chlorophenyl)({3-[({methyl[(4-methylphenoxy)acetyl]amino}acetyl)amino]phenyl}sulfonyl)amino]acetate;

tert-Butyl[(3-chlorophenyl)({3-[({methyl[(3-methylphenoxy)acetyl]amino}acetyl)amino]phenyl}sulfonyl)amino]acetate;

tert-Butyl[(3-chlorophenyl)({3-[({methyl[(2-methylphenoxy)acetyl]amino}acetyl)amino]phenyl}sulfonyl)amino]acetate;

tert-Butyl ((3-chlorophenyl){3-({[[(9H-fluoren-9-ylmethoxy)carbonyl](methyl)amino]acetyl}amino)phenyl]sulfonyl}amino)acetate;

tert-Butyl{(3-chlorophenyl)[(3-{[(methylamino)acetyl]amino}phenyl)sulfonyl]amino}acetate;

3-{[(2-tert-Butoxy-2-oxoethyl)(3-chlorophenyl)amino]sulfonyl}benzoic acid;

tert-Butyl[{[3-({[3-(benzylamino)-3-oxopropyl]amino}carbonyl)phenyl]sulfonyl}(3-chlorophenyl)amino]acetate;

tert-Butyl[(3-chlorophenyl)({3-[({3-oxo-3-[(2-phenylethyl)amino]propyl}amino)carbonyl]phenyl}sulfonyl)amino]acetate;

tert-Butyl[[(3-{[(2-{[(benzyloxy)carbonyl]amino}ethyl)amino]carbonyl}phenyl)sulfonyl](3-chlorophenyl)amino]acetate;

tert-Butyl[[(3-{[(3-{[(benzyloxy)carbonyl]amino}propyl)amino]carbonyl}phenyl)sulfonyl](3-chlorophenyl)amino]acetate;

tert-Butyl[({3-[({2-[(4-chlorobenzoyl)amino]ethyl}amino)carbonyl]phenyl}sulfonyl)(3-chlorophenyl)amino]acetate;

tert-Butyl{(3-chlorophenyl)[(3-{[(3,3-diphenylpropyl)amino]carbonyl}phenyl)sulfonyl]amino}acetate;

benzyl (2-{[3-({(3-chlorophenyl)[2-(cyclohexylamino)-2-oxoethyl]amino}sulfonyl)phenyl]amino}-2-oxoethyl)methylcarbamate;

Benzyl (2-{[3-({(3-chlorophenyl)[2-(isopropylamino)-2-oxoethyl]amino}sulfonyl)phenyl]amino}-2-oxoethyl)methylcarbamate;

Benzyl{2-[(3-{[(3-chlorophenyl)(2-{[2-(dimethylamino)ethyl]amino}-2-oxoethyl)amino]sulfonyl}phenyl)amino]-2-oxoethyl}methylcarbamate;

tert-Butyl[{[3-({[[(benzyloxy)carbonyl](methyl)amino]acetyl}amino)phenyl]sulfonyl}(4-chlorophenyl)amino]acetate;

tert-Butyl[{[3-({[[(benzyloxy)carbonyl](methyl)amino]acetyl}amino)phenyl]sulfonyl}(2-chlorophenyl)amino]acetate;

tert-Butyl[{[3-({[[(benzyloxy)carbonyl](methyl)amino]acetyl}amino)phenyl]sulfonyl}(phenyl)amino]acetate;

tert-Butyl[{[3-({[[(benzyloxy)carbonyl](methyl)amino]acetyl}amino)phenyl]sulfonyl}(3,5-dichlorophenyl)amino]acetate;

tert-Butyl{{[3-({[[(benzyloxy)carbonyl](methyl)amino]acetyl}amino)phenyl]sulfonyl}[3-(trifluoromethyl)phenyl]amino}acetate; and tert-Butyl[{[3-({[[(benzyloxy)carbonyl](methyl)amino]acetyl}amino)phenyl]sulfonyl}(3-cyanophenyl)amino]acetate.

8. A pharmaceutical composition, comprising: a pharmaceutically acceptable carrier and a compound of claim 1.

9. A pharmaceutical composition, comprising: a pharmaceutically acceptable carrier and a compound of claim 4.

* * * * *

UNITED STATES PATENT AND TRADEMARK OFFICE
CERTIFICATE OF CORRECTION

PATENT NO. : 7,504,431 B2  
APPLICATION NO. : 11/107218  
DATED : March 17, 2009  
INVENTOR(S) : Jon J. Hangeland et al.

Page 1 of 1

It is certified that error appears in the above-identified patent and that said Letters Patent is hereby corrected as shown below:

In the Claims:

Claim 7:
    Column 55, line 44, delete "of claim 1".

Signed and Sealed this
Second Day of August, 2011

David J. Kappos
*Director of the United States Patent and Trademark Office*